US011045116B1

(12) United States Patent
Martin

(10) Patent No.: US 11,045,116 B1
(45) Date of Patent: Jun. 29, 2021

(54) ENHANCED DETERMINATION OF CADENCE FOR CONTROL IN MOBILE

(71) Applicant: David Martin, San Francisco, CA (US)

(72) Inventor: David Martin, San Francisco, CA (US)

( * ) Notice: Subject to any disclaimer, the term of this patent is extended or adjusted under 35 U.S.C. 154(b) by 60 days.

(21) Appl. No.: 15/706,651

(22) Filed: Sep. 15, 2017

(51) Int. Cl.
*A61B 5/11* (2006.01)
*H04W 4/02* (2018.01)
*G01S 19/25* (2010.01)
*G01C 22/00* (2006.01)

(52) U.S. Cl.
CPC ............ *A61B 5/112* (2013.01); *G01C 22/006* (2013.01); *G01S 19/25* (2013.01); *H04W 4/027* (2013.01)

(58) Field of Classification Search
CPC ........ A61B 5/112; H04W 4/027; G01S 19/25; G01C 22/006
USPC ........................................... 600/595; 702/160
See application file for complete search history.

(56) References Cited

U.S. PATENT DOCUMENTS

| | | | | |
|---|---|---|---|---|
| 8,021,270 B2* | 9/2011 | D'Eredita | ............... | G16H 50/20 482/8 |
| 9,599,819 B2* | 3/2017 | Alaniz | ..................... | G06F 3/011 |
| 2009/0124938 A1* | 5/2009 | Brunner | ............... | A61B 5/1038 600/595 |
| 2009/0137933 A1* | 5/2009 | Lieberman | ............ | A61B 5/1036 600/595 |
| 2010/0053322 A1* | 3/2010 | Marti | ...................... | G06F 3/011 348/135 |
| 2010/0191697 A1* | 7/2010 | Fukumoto | ............. | A61B 5/1116 706/54 |
| 2011/0009241 A1* | 1/2011 | Lane | ................... | A63B 24/0087 482/8 |
| 2011/0313705 A1* | 12/2011 | Esser | ..................... | A61B 5/112 702/104 |
| 2013/0041291 A1* | 2/2013 | Soubeyrat | ............ | A61B 5/1038 600/595 |
| 2013/0069862 A1* | 3/2013 | Ur | ............................. | G06F 3/01 345/156 |
| 2013/0225288 A1* | 8/2013 | Levin | ..................... | A63F 13/23 463/31 |
| 2014/0275850 A1* | 9/2014 | Venkatraman | ....... | A61B 5/0002 600/301 |
| 2014/0288679 A1* | 9/2014 | McNamee | ........... | G11B 27/005 700/91 |
| 2014/0316305 A1* | 10/2014 | Venkatraman | ........ | A61B 5/1112 600/595 |
| 2015/0009348 A1* | 1/2015 | Vartanian | ........... | H04N 5/23206 348/211.3 |
| 2015/0018013 A1* | 1/2015 | Martin | .................. | H04W 4/027 455/456.3 |
| 2015/0100141 A1* | 4/2015 | Hughes | ................. | A61B 5/1118 700/92 |

(Continued)

*Primary Examiner* — Steven O Douglas

(57) ABSTRACT

Methods for controlling in real time an aspect of a process in a mobile or wearable device with a cadence of the device user are described, where the cadence of the device user is determined with an update frequency greater than the user's step frequency, and the controlling is also performed with an update frequency greater than the user's step frequency. For example, the determination of the user's cadence may leverage a combination of frequency and time techniques, with the analysis of, for instance, substantial orientation changes experienced by the device, or the detection of abrupt changes in the user's cadence.

99 Claims, 12 Drawing Sheets

(56) References Cited

U.S. PATENT DOCUMENTS

| | | | | |
|---|---|---|---|---|
| 2015/0133820 A1* | 5/2015 | Zohar | ............... | A61B 5/1118 |
| | | | | 600/595 |
| 2015/0213729 A1* | 7/2015 | Rhea | ............... | G06F 19/3481 |
| | | | | 434/247 |
| 2015/0362520 A1* | 12/2015 | Wells | ............... | G01C 19/00 |
| | | | | 702/141 |
| 2015/0363965 A1* | 12/2015 | Wells | ............... | G06F 3/017 |
| | | | | 345/419 |
| 2016/0034817 A1* | 2/2016 | Ali | ............... | H04M 1/72569 |
| | | | | 706/46 |
| 2016/0038088 A1* | 2/2016 | Lari | ............... | A61B 5/6898 |
| | | | | 600/595 |
| 2016/0113550 A1* | 4/2016 | Martin | ............... | A61B 5/6898 |
| | | | | 600/595 |
| 2016/0166180 A1* | 6/2016 | Martin | ............... | A61B 5/112 |
| | | | | 702/141 |
| 2016/0189423 A1* | 6/2016 | Kaeser | ............... | G06F 3/012 |
| | | | | 345/420 |
| 2016/0271451 A1* | 9/2016 | Wu | ............... | G06K 9/00342 |
| 2016/0317866 A1* | 11/2016 | Fung | ............... | A63B 24/0003 |
| 2017/0188897 A1* | 7/2017 | Thein | ............... | A61B 5/7221 |

* cited by examiner

ENHANCED DETERMINATION OF CADENCE FOR CONTROL IN MOBILE

BACKGROUND

Field

This application relates to mobile and wearable devices, specifically to methodologies to leverage user's gait characteristics.

Discussion of Related Art

Common methods to obtain cadence by means of sensors embedded within mobile or wearable devices make use of thresholds, and detect steps when the value of a sensor signal reaches said thresholds. In order to achieve an accuracy improvement, the use of adaptable thresholds has also been proposed. Nevertheless, most of those approaches focus their analysis on the time domain, and although some methods make use of frequency analysis (e.g. using FFT to obtain the fundamental frequency of the signal), their algorithms still rely on thresholding in the time domain, making them prone to errors, especially with weak or noisy motion signals typical of walking. Recent studies with commercially available devices show large errors in the determination of the user's cadence, and those errors increase as the walking velocity decreases. In fact, considerable inaccuracies at low speeds may have important implications in health care applications. Consequently, there is a need for an enhanced methodology to accurately determine the cadence of mobile or wearable device users, and enable a new field of applications not possible with existing methodology.

DETAILED DESCRIPTION OF EMBODIMENTS OF THE INVENTION

Although the following text sets forth a detailed description of numerous different embodiments, it should be understood that the legal scope of the description is defined by the words of the claims set forth at the end of this disclosure. The detailed description is to be construed as exemplary only and does not describe every possible embodiment since describing every possible embodiment would be impractical, if not impossible. Numerous alternative embodiments could be implemented, using either current technology or technology developed after the filing date of this patent, which would still fall within the scope of the claims.

It should also be understood that, unless a term is expressly defined in this patent using the sentence "As used herein, the term ' 'is hereby defined to mean . . . "or a similar sentence, there is no intent to limit the meaning of that term, either expressly or by implication, beyond its plain or ordinary meaning, and such term should not be interpreted to be limited in scope based on any statement made in any section of this patent (other than the language of the claims). To the extent that any term recited in the claims at the end of this patent is referred to in this patent in a manner consistent with a single meaning, that is done for sake of clarity only so as to not confuse the reader, and it is not intended that such claim term be limited, by implication or otherwise, to that single meaning.

Some inventive functionality and inventive principles may be implemented with or in software programs or instructions and integrated circuits (ICs) such as application specific ICs. In the interest of brevity and minimization of any risk of obscuring the principles and concepts according to the present invention, discussion of such software and ICs, if any, is limited to the essentials with respect to the principles and concepts within some of the embodiments.

Figure 1A:
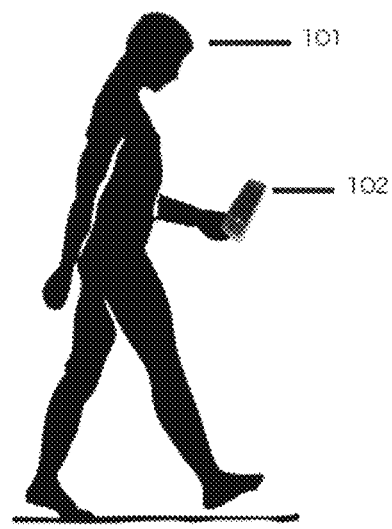
FIG. 1A represents an example of mobile device user walking with the device.
Figure 1B:
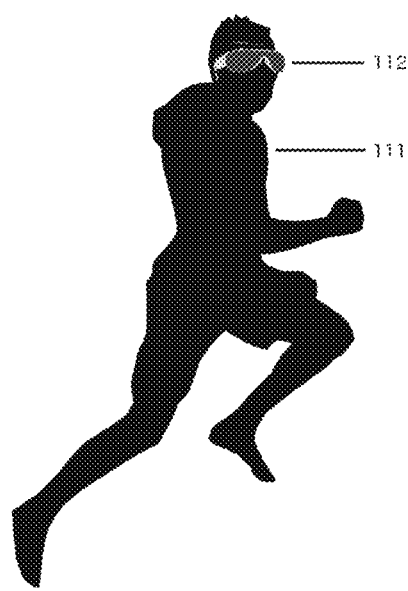
FIG. 1B represents an example of wearable device user running with the device.

FIG. 1A represents an individual, (101), walking with a mobile device, (102). In some embodiments, individual (101) may be performing any kind of walking, jogging, running, sprinting, or any other type of gait activity. In other embodiments, individual (101) may be performing any kind of activity. In some embodiments, (101) could be a human, a robot, or a non-human animal, while (102) could be any type of mobile, wearable or any other type of device (capable of being positioned in any part of the body or any where), with any combinations thereof also possible. By way of example, and not limitation, (102) may represent a smartphone held in the hand or hands while individual (101) walks looking at its screen. In some embodiments, device (102) could be positioned in any pocket of individual (101), or held in any hand while walking without facing the individual (by way of example, and not limitation, when the individual does not look at the device screen), or placed in any type of clothing or any kind of bag or accessory brought by the individual. In some embodiments, device (102) could be positioned, placed or in any way attached to any part of the individual's body or accessories. By way of example, and not limitation, in some embodiments (102) may represent any type of hands-free device, virtual reality device, eyewear or glasses that individual (101) is wearing in any way attached or positioned on his/her face, head, or any other place of his/her body or accessories. In this sense, FIG. 1B represents an example of one embodiment in which individual (111) is running while wearing a device in the form of glasses (112). In some embodiments (112) may represent any type of virtual reality device, eyewear, glasses or any other type of wearable or mobile device that individual (111) is wearing in any way attached or positioned on his/her face, head, or any other place of his/her body or accessories, and individual (111) may be performing any kind of walking, jogging, running, sprinting, or any other type of gait activity. In other embodiments, individual (111) could be performing any kind of activity. In general, any examples/embodiments applicable to (101) and (102), are applicable to (111) and (112) respectively, and vice-versa, with any variations and/or combinations also possible.

Figure 1C:
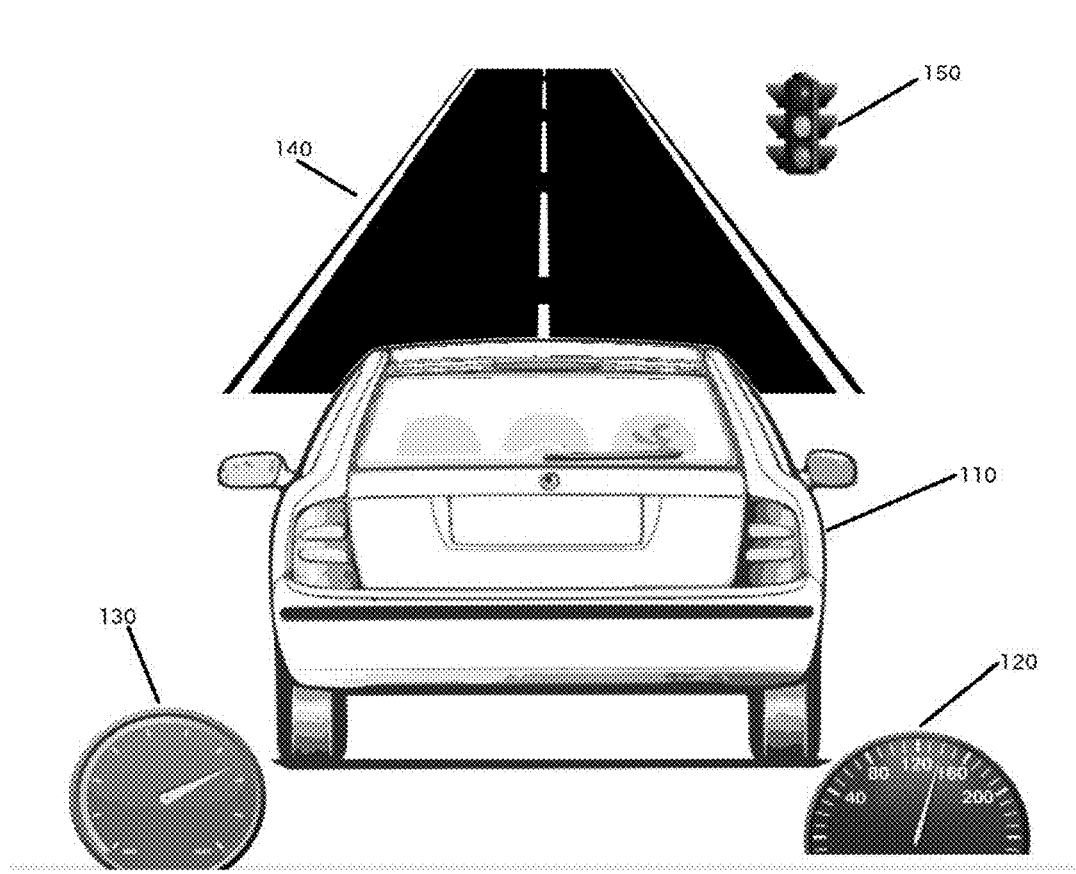
FIG. 1C illustrates an example of virtual environment displayed on the mobile or wearable device according to one embodiment.

In some embodiments, FIG. 1C may illustrate an example of screenshot of the display of devices (102) or (112), representing a virtual environment with which the individual (101) or (111) may interact. By way of example, and not limitation, the display may show a car (110) moving along a road (140) with some elements such as traffic lights (150). Moreover, the display may also show some dashboard elements such as (120) or (130) to indicate certain magnitudes, variables or metrics of any kind. In some embodiments, dashboard elements (120) and/or (130) may show indications applicable to the element (110) and/or to individual (101) or (111) and/or to device (102) or (112), and/or combinations thereof, including, by way of example, and not limitation: velocity, power, fuel, oil, pressure, temperature, battery, lights, stability, distance, direction, acceleration, stride length, heart rate, perspiration rate, blood pressure, glucose level, or any other kind of magnitude, variable or metric measurable in any way directly by device (102) or (112), or by any other devices and/or sensors connectable in any way to device (102) or (112), or by any other devices and/or sensors to which individual (101) or (111) could somehow have access, or by any other devices and/or sensors to which element (110) could have access in any form in reality or in the virtual environment being represented. In some embodiments, the display may present comparisons of any of the user's current gait/motion characteristic with his/her own previous ones, with other users' ones, or with any type of model or information, and/or combinations thereof.

In a particular embodiment, any number of dashboard elements (120) and/or (130) may be displayed; in other embodiments, these and/or any other elements may not be displayed, while the presence of any or all of these elements may be temporary depending on a plurality of criteria, such as device power management, adaptation of screen space to particular conditions, user's choice, or any other reason. In some embodiments, the properties of any or all the elements displayed may be fixed, while in other embodiments, the properties of any or all the elements displayed may vary depending on a plurality of criteria, such as device power management, adaptation of screen space to particular conditions, user's choice, results of interaction, or any other reason. By way of example without limitation, properties in the elements that may be varied at any time and for any reason include, shape, color, update rate, purpose, ways of indication (needle, bar, line, etc.), location in the screen, transparency, capability of being interactive in any way, degree of interaction, or any other feature.

In some embodiments, element (110) may represent any means of transportation, including by way of example without limitation, any transportation means by ground (e.g. car, truck, van, train, horse pulled wagon, motorcycle, bicycle, skateboard, snowboard, sledge, etc.), any transportation means by air (e.g. airplane, military fighter, rocket, balloon, glider, etc.), any transportation means by space (e.g. spaceship, rocket, etc.), any transportation means by water (e.g. ship, boat, kayak, submarine, etc.), or any other tool, device or object of any nature capable of moving in any way through any means, including hybrids and/or mixtures and/or combinations thereof; in some embodiments, any aspect or property related to element (110) may be controlled by any characteristic of the user's movement or gait (including cadence).

In other embodiments, element (110) may represent any kind of human being (including him/herself) or groups of human beings, or any kind of non-human beings or objects of any nature and form, including, by way of example without limitation, any type of animal or groups of animals, any type of robots, any type of virtual, imaginary or fantasized being or object, of any nature, shape, color, size or any other properties, and any mixtures and/or combinations thereof.

In some embodiments, one or more elements (110) may be displayed with the same or similar properties; in other embodiments with more than one element (110), they may have different properties; in other embodiments, the properties of one or more elements (110) may be varied at any time depending on a plurality of criteria, including, by way of example without limitation, user's choice, results of interaction, device power management, adaptation of screen space to particular conditions, or any other reason. In some embodiments, the properties that may be varied include, by way of example without limitation, shape, color, form, nature, purpose, ways of movement, different capabilities (including capability of being interactive in any way), location in the screen, transparency, degree of interaction, or any other feature or property.

In some embodiments, element (140) may represent a road along which element (110) moves, or any kind of entity of any nature capable of allowing any type of movement; in other embodiments, element (140) may represent any kind of means, including by way of example and not limitation, any kind of ground road, highway, path, snow covered field, ice platform, river, cross country fields, outer space, racing means and/or environments of any type and nature, any kind of means of any nature (e.g. solid, liquid, gas, plasma) where any element (110) may perform any type of movement, or any kind of real, imaginary or fantasized entity or substance, and any mixture and/or combinations thereof.

In some embodiments, element (150) may represent traffic lights or any kind of object or being of any nature capable of influencing, regulating, monitoring and/or controlling the movement of element (110) in any way; in other embodiments, element (150) may represent any type of object or being of any nature capable of catching the attention of individual (101) or (111); in other embodiments, element (150) may represent any type of object or being of any nature capable of interacting with element (110) and/or individual (101) or (111) in any way. By way of example and not limitation, in some embodiments element (150) may represent any type of element (similar or different to any type of element (110)) moving in the same environment and being able to interact with element (110) destructively (e.g. enemy car shooting at wheels, enemy zombie in the middle of the road, enemy truck spilling oil on the road, etc.) or constructively (e.g. safety truck for rescue operations, friendly car offering prizes, friendly gnome offering rewards, etc.). In some embodiments, interactions of some element (150) with individual (101) or (111) may include, by way of example without limitation, acoustic signals, visual messages, vibration of the device for a certain amount of time, etc. In other embodiments, element (150) may represent any type of object or being of any kind or nature, including, by way of example without limitation, obstacles, man waving flag indicating distance traveled, road signs, etc. In other embodiments, the number of elements (150) displayed on the screen may be any (including more than one), and they may have any nature (including real, virtual, fantasized, etc.) and/or properties, including mixtures and/or combinations thereof.

Figure 2A:
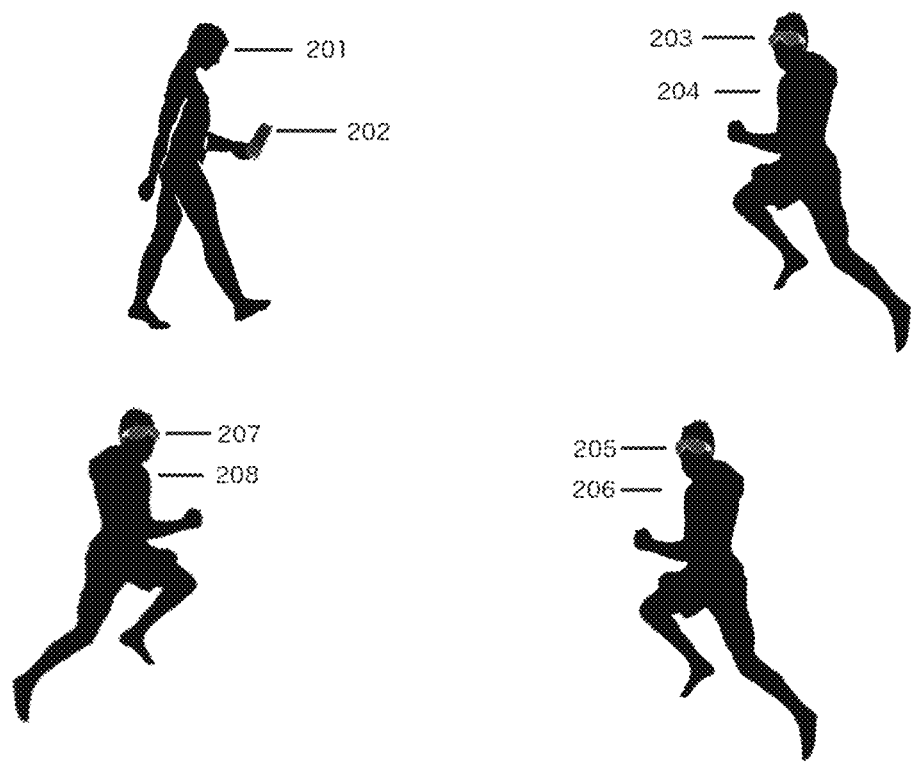
FIG. 2A represents an example of mobile and/or wearable device users performing some gait activity with their devices in a networking environment.

FIG. 2A represents an example of an embodiment in which four individuals (201), (204), (206), (208) participate in a networking environment; in this particular embodiment, each individual has one device: individual (201) is walking and has device (202), which may represent a smartphone, phablet, tablet, or any other type of device, including by way of example without limitation, any of the types of devices that (112) and/or (102) may represent. Individual (204) is running and has device (203), which may represent any type of electronic glasses, a virtual reality device, or any kind of wearable device worn on any part of the body, or any other type of device, including by way of example without limitation, any of the types of devices that (112) and/or (102) may represent. In a similar way, individuals (206) and (208) are running and wearing their own devices (205) and (207) respectively, which again could be any of the types of devices that (112) and/or (102) may represent.

In other embodiments, the number of individuals participating in a networking environment may be any, each one of the individuals may have any number of devices of any type positioned/attached/located/worn on any place, and each one of the individuals may perform any type of walking, jogging, running, sprinting, or any other type of activity regardless of the type of device and/or their position. In some embodiments, the individuals (201), (204), (206), (208) and/or any other number of individuals participating in a networking environment, may all be physically located next to each other in approximately the same location. In other embodiments, one or more (or all) individuals may be physically located in different and/or distant locations. By way of example without limitation, each individual could be in a different city.

In some embodiments, communication between devices (202), (203), (207), (205) and/or others to enable the networking environment may leverage any means, including, by way of example without limitation, any wireless and/or any other type of communications technology, such as LTE, UMTS, GSM, WiFi, Bluetooth and/or any other kind and combinations thereof. In some embodiments, the means of communications and/or their properties may be varied at any time and depending on any reason. These changes and/or choices may depend on a plurality of factors, including, by way of example without limitation, network availability, physical proximity of individuals, power management, communication efficiency, specific usage plans, etc. In some embodiments where the devices are in close proximity, they may communicate directly with each other using any kind of short-range communications technology or any other type of means and/or technology without the need to relay on other communications networks elements such as cellular base stations or WiFi access points.

Figure 2B:
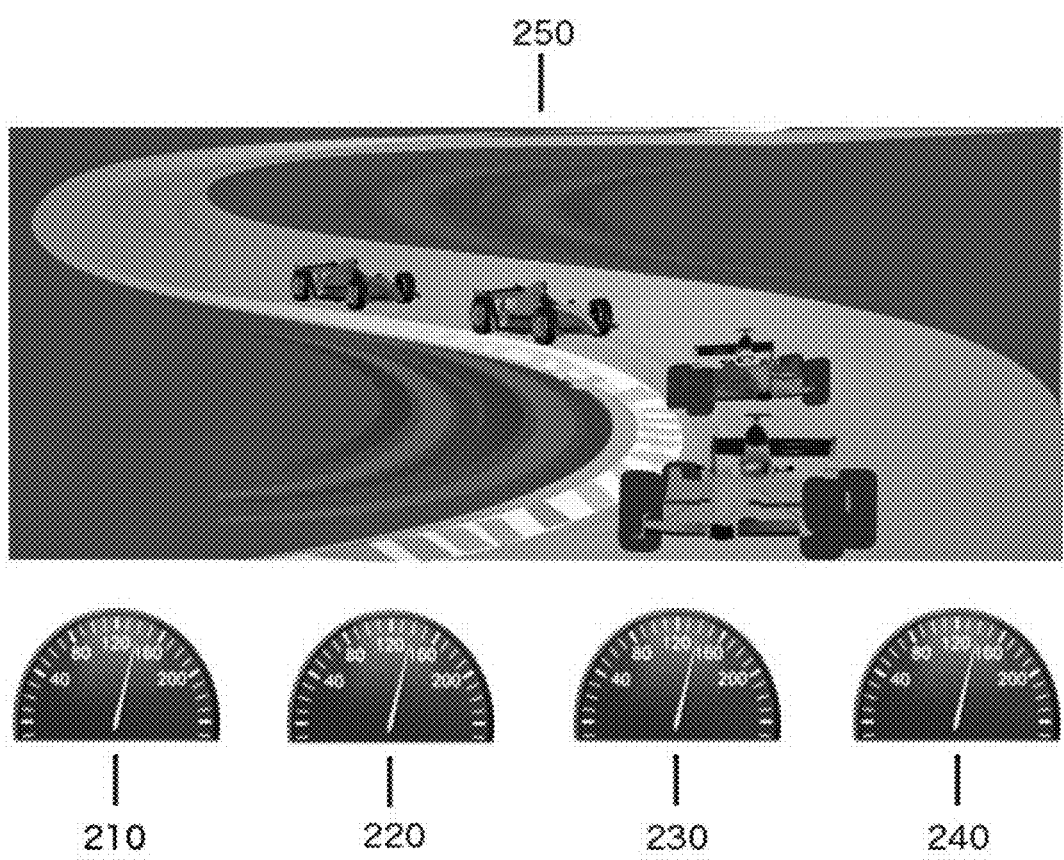
FIG. 2B illustrates an example of virtual environment displayed on the mobile and/or wearable devices in a networking environment according to one embodiment.

FIG. 2B represents an example of an embodiment illustrating an example of screenshot of the display of any or all of the devices (202), (203), (207) or (205). In a particular embodiment corresponding to a networking environment such as the one represented in FIG. 2A, FIG. 2B may represent an example of screenshot seen by individuals (201), (204), (206) and (208) in the display of any or all of their devices.

In some embodiments, the networking virtual environment illustrated in FIG. 2B is an extension of the virtual environment described in FIG. 1C, in which the number of individuals represented (each element (110) in FIG. 1C, corresponding to each one of the cars illustrated in scene (250)) has been adapted to account for the number of individuals participating in the networking environment (e.g. individuals (201), (204), (206) and (208) in FIG. 2A, instead of just individuals (101) or (111) in FIG. 1A or FIG. 1B). Also, the number and characteristics of elements (120) and/or (130) in FIG. 1C, corresponding to any number and type of elements (210), (220), (230) and/or (240) illustrated in FIG. 2B, have been extended/adapted to account for the number of individuals participating in the networking environment. For the shake of clarity and simplicity of FIG. 2B, elements and/or details that may be further specified/included in any part or position of said FIG. 2B, have been avoided. However, any element described for FIG. 1C ((110), (120), (130), (140), (150)) may be included in any part or position of FIG. 2B, in any number and with any characteristic. Moreover, any other elements that may have not been described (for the shake of brevity some elements may have not been mentioned/described/specified), may also be included in both FIG. 1C and/or FIG. 2B (and/or in their respective elements); these additional elements and/or any combination of them and/or the elements already described, may be included in any number, with any characteristics, with any purpose, and in any combination thereof in any of FIG. 1C and/or FIG. 2B. In some embodiments, by way of example without limitation, the networking virtual environment represented in FIG. 2B and the virtual environment represented in FIG. 1C may illustrate/represent any kind of real, imagined or fantasized environment in any conditions and with any characteristics.

In some embodiments, the networking environment in which individuals (201), (204), (206) and (208) participate may be intended to generate a representation of a virtual environment in the displays of their devices, which would be shared by all individuals (201), (204), (206) and (208) regardless of their physical location, type of device, positioning of the device, activity that the individuals are performing, or any other condition. In a particular embodiment represented in FIG. 2B, individuals (201), (204), (206) and (208) from FIG. 2A could be performing the same activity (e.g. walking, jogging, running) and each one of those individuals would be represented in the particular virtual environment illustrated in FIG. 2B by each one of the cars appearing in scene (250), where a road is also represented for the cars to move along it. In other words, regardless of the physical location and/or any other conditions of individuals (201), (204), (206) and (208), they may all share the same virtual environment represented in FIG. 2B displayed in their devices, and appear in the same scene (250), where each one of the individuals may be represented by each one of the cars displayed in scene (250), and each one of individuals (201), (204), (206) and (208) is assigned dashboard elements (210), (220), (230) and (240) respectively, equal or similar to any of those dashboard elements (120) or (130) in FIG. 1C.

In some embodiments, scene (250) may be composed of any or all of the elements described in FIG. 1C, in any number, with any characteristics and with any variations and/or combinations thereof. In some embodiments, elements (210), (220), (230) and (240) may represent any number and type of elements (120) and/or (130) from FIG. 1C, again, with any characteristics, variations and/or combinations thereof.

In some embodiments, the different individuals participating in the networking environment and/or elements representing them (e.g. the different individuals in FIG. 2A and/or the different cars in scene (250) in FIG. 2B) may interact with any other element in the networking virtual environment, including the other individuals and/or their representations in the networking virtual environment. By way of example without limitation, in some embodiments, individuals and/or elements representing individuals in the networking environment may by themselves, or with the help of any kind of real and/or virtual tool or device, trigger/execute any kind of action influencing in any way any or all of the other elements in scene (250) (including the elements representing individuals) and/or any or all of the individuals themselves; in this sense, a set of non-limiting examples are included next: a car representing an individual in scene (250) may crash against another car in the same scene, or use some weapon against other cars; or a car in scene (250) may show a visual message aimed at some specific individual; or an individual participating in the networking virtual environment may select an option to disrupt the engine of any of the cars in scene (250); or an individual participating in the networking virtual environment may select an option to send an acoustic, visual, mechanical (e.g. vibration) or any other nature signal directly to any other individual's device; or any other kind of variations and/or combinations thereof.

In some embodiments, all the individuals participating in the networking environment are assumed or expected to perform the same gait activity or activities, and their experiences in the virtual environment will be influenced by characteristics/metrics/variables of their gait activities. In other embodiments, the individuals participating in the networking environment may be carrying out any type of activity (different individuals may also perform different activities) and the type of activity performed by the individuals may influence their representation in scene (250) and/or their overall experience in the virtual environment. In other embodiments, the individuals participating in the networking environment may be carrying out any type of activity regardless of their experiences and/or representation in the virtual environment. Any variations and/or combinations are also possible.

In some embodiments, the individuals participating in the networking environment may be moving in their real environment in any direction and/or combinations of directions regardless of their experiences and/or representation in the virtual environment. In other embodiments, the real environment direction of movement of the individuals participating in the networking environment may influence their experiences and/or representation or any other aspect in the virtual environment. The same applies to any individuals from FIG. 1A and FIG. 1B, who may or may not be participating in a networking environment.

In some embodiments, the individuals participating in the networking environment may be moving in their real environment with some measurable characteristics (including, by way of example without limitation, speed, stride length, cadence, acceleration) that may influence their experiences and/or representation in the virtual environment in any way; the same is applicable in cases where an individual is on his/her own interacting with any virtual environment as described by any or all of FIG. 1A, FIG. 1B, and FIG. 1C. In other embodiments, the individuals participating in the networking environment may be moving in their real environment with some measurable characteristics (including, by way of example without limitation, speed, stride length, cadence, acceleration) that may not influence their experiences and/or representation in the virtual environment; the same is applicable in cases where an individual is on his/her own interacting with any virtual environment as described by any or all of FIG. 1A, FIG. 1B, and FIG. 1C.

In some embodiments, all devices participating in the networking environment will display the same representation of the virtual environment; in some embodiments, the representation of the virtual environment in all devices will be the same or similar, with possible adaptations to any specificity of the devices (by way of example without limitation: any adaptation due to availability (or lack of availability) of hardware in the device, any adaptation due to operating system or any software characteristics in the device, any scaling to adapt to the display size of the device, etc.); in some embodiments, any or all of the devices participating in the networking environment may have a different representation of the virtual environment, depending on different criteria (including, by way of example without limitation, display size, power management, user's choice, activity type, activity characteristics, device positioning, user location, or any other reason and/or combinations thereof).

In some embodiments, all the individuals participating in the networking environment have the same representation in the virtual environment (e.g. all individuals in the networking environment are represented in the virtual environment by the same type of cars, or by the same type of motorcycles, or by the same type of airplanes, etc.). In other embodiments, any or all of the individuals participating in the networking environment may be represented in the virtual environment by different types of elements (e.g. one individual may choose to be represented in the shared networking virtual environment by a car, while other individual may choose to be represented in the shared networking virtual environment by a motorcycle, other individual may choose to be represented in the shared networking virtual environment by a leopard, other individual may choose to be represented in the shared networking virtual environment by an athlete, etc.). In other embodiments, any combinations of the previously described possibilities of representation of individuals in any virtual environment are applicable to any type of environment, including, by way of example without limitation, the possibility of selecting and/or changing the representation of any or all of the individuals in any way, at any time and because of any reason.

In some embodiments, the presentation of any or all of the elements (and/or any information about them) in any environment may be scalable and/or scrollable and/or modifiable and/or sortable and/or organizable in any way depending on any reason. By way of example without limitation, a very large number of individuals participating in a networking environment may trigger a process to organize information about the individuals in a scrollable view.

In some embodiments, the properties of any or all the elements described or any other features of any embodiment may vary depending on a plurality of criteria, such as device power management, adaptation of screen space to particular conditions, user's choice, results of interaction, or any other reason. By way of example without limitation, the properties or features that may be varied at any time and for any reason include: shape, color, update rate, purpose, location in the screen, transparency, capability of being interactive in any way, degree of interaction, or any other and combinations thereof. Also, any descriptions, modifications and/or combinations thereof are applicable to any of the figures, embodiments and/or any of their elements.

Figure 3:
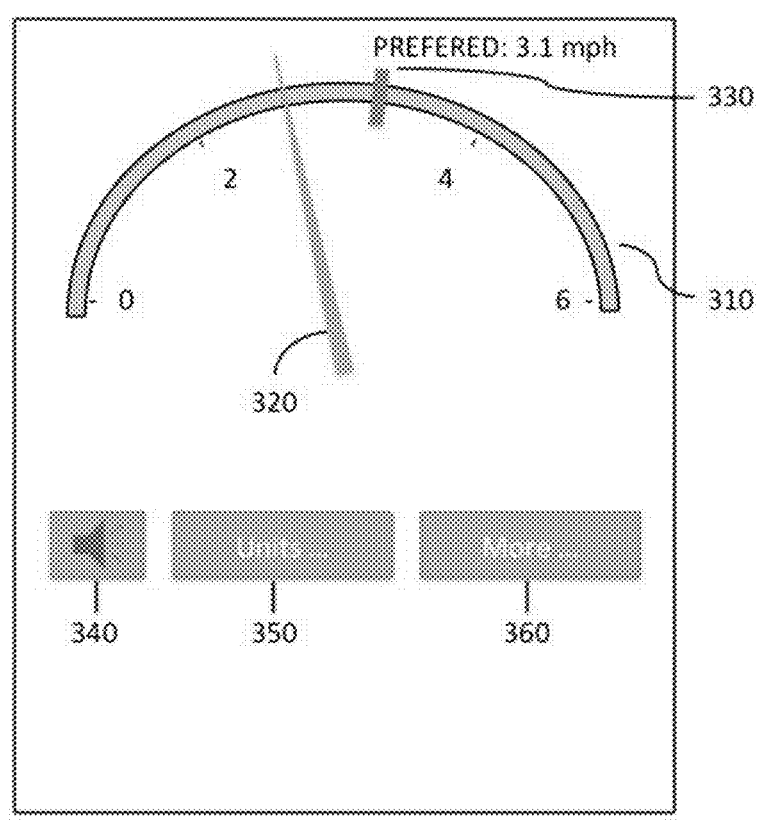
FIG. 3 shows an example of an embodiment of the presentation of contextual information on a mobile and/or wearable device.

In some embodiments, any contextual information may be displayed directly on the user's device display. By way of example and not limitation, the velocity of the user may be displayed in real time (typically, fractions of a second) on the mobile device display as shown in FIG. 3, which illustrates an example of the many possibilities. Some embodiments may present the real time value and evolution of the contextual information on the mobile device. Other embodiments may display the contextual information on an external managing or monitoring entity, which may comprise computing and storing resources. Other embodiments with different configurations and/or combinations thereof are also possible. In some embodiments, a semicircular scale may be used to represent the velocity magnitude (310), and it may be calibrated in different and adaptable units and values depending on context. By way of example and not limitation, walking velocities may be represented from 0 miles-per-hour (mph) to 6 mph. In addition, the scale may include a variety of features, such as the preferred walking velocity (330) or others. These features may be average values or personalized values for each particular user. Other embodiments may use other types of features and/or combinations thereof. By way of example and not limitation, some embodiments may use a semicircle with different colors representing velocity values.

In some embodiments, the representation of a moving needle (320) may be leveraged to indicate the real time velocity of the user. In other embodiments, other representations may be leveraged to indicate the real time velocity of the user, including but not limited to, the surface of a varying semicircle whose angle grows from 0 degrees to 180 degrees depending on the velocity. In other embodiments, semi-arcs or other types of geometries, shapes, sizes, figures, etc. may also be leveraged. In some embodiments, combinations geometries and/or color may also be leveraged to display the velocity information. In some embodiments, the presentation of information to the user or to any type of managing or monitoring entity may be performed personalized and in any of several ways including, by way of example, and not limitation, visual, acoustic, etc. For example, a button for sound (340) may be used to enable or disable the acoustic delivery of contextual information. This button may also be leveraged to enable or disable playing music or other encouraging sound in the background, or to trigger an out-loud-reader mechanism to read-out-loud contents on the display (e.g. text from a website, messages received from friends, etc.) when predetermined and/or selectable thresholds or levels on the user's velocity or general context are reached. Another button may be used to change the units of the velocity (350), for example, meters per second, kilometers per hour, etc. In some embodiments, automatic localization or other means may be leveraged to infer the country of the user and automatically adapt units, language, and other variables. Additional buttons (360) may also be employed for other purposes, including but not limited to, displaying a time evolution of the user velocity, dynamics, or general context over a selected or available period of time, allow personalized calibration, set preferences, etc.

In some embodiments, any element(s) described for any figure or embodiment may be optional, or any of them and any other additional element(s) with any features and/or combinations thereof, may also be included in any fashion in any figure or embodiment.

Figure 4:
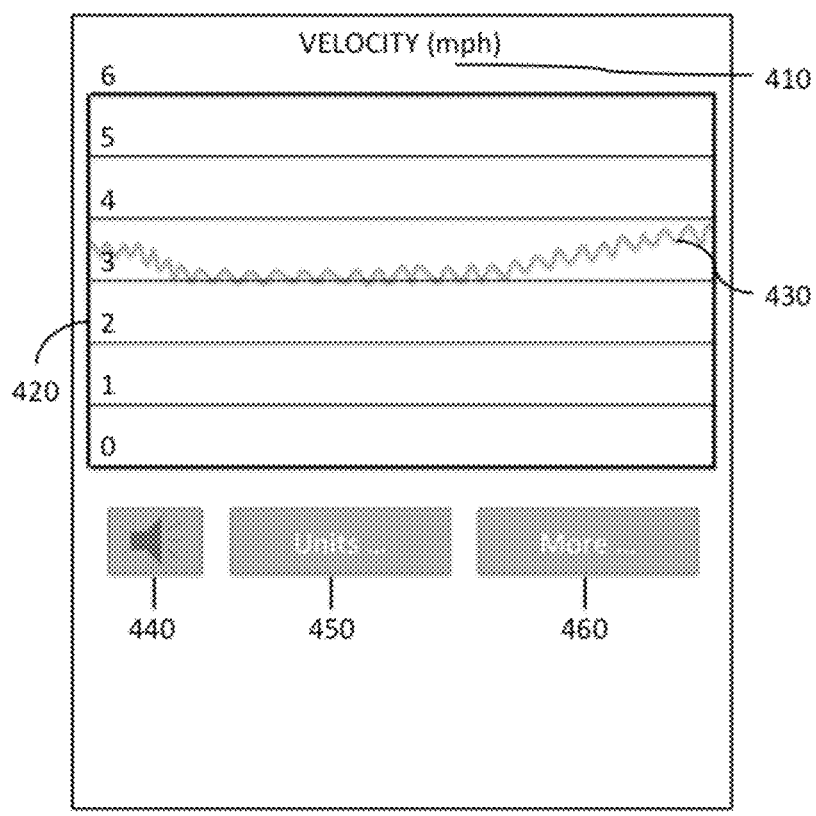
FIG. 4 shows an example of another embodiment of the presentation of contextual information on a mobile and/or wearable device.

FIG. 4 represents an embodiment of a representation of the user's velocity; in other embodiments, any other contextual information and/or gait characteristic or attribute (e.g. stride length, cadence, calories burned, etc. and combinations thereof) or related information may be represented. In a particular embodiment, real-time feedback and/or comparisons with other users and/or devices may also be allowed in any fashion.

In some embodiments, element (410) is an optional label and may provide the name of the gait characteristic being displayed together with any form of any possible units in which it may be measured (if applicable), or any other type of information of any nature, including abbreviations; particular examples may include: mph, miles per hour, kmh, kilometer hour, m/s, meter per second, etc. In other embodiments, if this label is included, depending on a variety of circumstances/conditions/choices, it may present any type of statements (e.g. "velocity (kmh)", "speed (mph)", "speed (kmh)", "stride length (m)", "stride length (ft)", etc.), forms, shapes, positions, nature (e.g. any picture, icon, multimedia element, etc. and combinations thereof), or any other property and/or combinations thereof. In some embodiments, element (420) is also optional and it represents chart axes or grid for clarity purposes (any of its components is also optional and may have any characteristic); in some embodiments, the vertical axis may be scaled in any way depending on the gait characteristic being displayed, and hold a set of representative figures together with any type of unit, statement, or any other element of any nature, form, or any other characteristic, and arranged/aligned/distributed in any way; in a particular embodiment, the vertical axis is scaled from 0 to 6 in consecutive numbers (representing units of velocity in miles per hour), and horizontal lines may cross the chart for each one of the presented numbers.

In some embodiments, the scale may additionally include a variety of features, such as the preferred walking velocity or others. These features may be average values or personalized values for each particular user. Other embodiments may use any other types of features and/or combinations thereof. In other embodiments, any or all of the horizontal bars and/or numbers along the vertical axis and/or any other element may be optional (e.g. it may not be displayed at any time for any reason) and if they are displayed, any or all of the referred elements or any other of any type that may also be added, may present any properties/features and combinations thereof.

Element (430) represents the measurement of the gait characteristic or attribute or any other related information being displayed. In a particular embodiment, it is a continuous line or curve (linking points ordered in time, each point corresponding to each measurement of the gait characteristic, e.g. velocity) freely following the measurements, having up to a predetermined threshold in the number of points, and accepting a new point to be displayed appended in a continuous form to the right edge of the curve every time a new measurement arrives. When the threshold in the number of points is reached, every time a new measurement arrives, the first point from the left edge (which in this embodiment represents the oldest measurement) is discarded, and the rest of points (except for the new one included at the right edge) are offset one position towards the left, thus giving the impression of a continuous flow of points following the arriving measurements. In some embodiments, the threshold in the maximum number of points in element (430) may be set to a fixed amount (e.g. a hundred or any other number), while in other embodiments it may be variable and depend on a variety of factors/circumstances/conditions, user's choices or any other reason. In some embodiment, any other type of indication and combinations thereof may be used instead of simple points or dots placed at the actual measurement value, such as, by way of example without limitation, any number of stars, squares, diamond shaped icons, any other type of polygon/icon/drawing/entity/element, any type of dotted lines/curves, any type of line/curve from any edge of the chart (or any other place) to the actual measurement value, any type of rectangle or any other polygon, icon, drawing, entity, element covering an area from any edge of the chart (or any other place) to the actual measurement value, or any other element(s) with any properties distributed and/or organized in any way, including any modifications and/or combinations thereof. In some embodiments, the indications may represent any type of information, including by way of example without limitation, the actual raw measurement of the gait characteristic being displayed, any value derived from the raw measurement or from any group of measurements (e.g. mean, standard deviation, etc.), or any other value, information, processed data or any other element in any way related with the gait characteristic and combinations thereof.

In some embodiments, the frequency at which a new point (or any indication of any type corresponding to measurements or any other data) is introduced in element (430) may be the frequency at which a new measurement is generated. In a particular embodiment presenting (by way of example) velocity, the use of (by way of example) methodology based on the application of the wavelet transform to the acceleration signal, would allow a new measurement every time a new acceleration value is available; consequently, the frequency at which a new measurement is generated may be equal to the accelerometer sampling frequency; in other words, the frequency at which the gait characteristic is updated may be equal to the accelerometer sampling rate, which in some embodiments may be higher than the user's step frequency. In some embodiments, other frequencies (lower or higher) may also be possible making use of different techniques, including by way of example without limitation, the use of any extra device, hardware, software, up sampling, down sampling, filtering, or any other techniques, tools and/or methodologies and any variations and/or combinations thereof. By way of example without limitation, in some embodiments the update frequency for the gait characteristic may be 60 Hz or 120 Hz depending on device hardware and other circumstances/conditions/choices, therefore achieving an enhanced real-time presentation of information (and user experience) in comparison with other methods with lower update rates; in some embodiments, when the user's step frequency is below 1 Hz (e.g. 0.5 Hz), the update rate may also be chosen just above the user's step frequency (e.g. 0.6 Hz), or above 1 Hz, or set as the accelerometer sampling rate (e.g. 60 Hz or 120 Hz) to enhance the real-time presentation of information (and user experience); other embodiments may choose any other update frequency or characteristic by modifying any settings, conditions, and/or choices of the referred and/or any other method. Other embodiments may employ any modification to any aspect previously mentioned, and/or combinations thereof.

In some embodiments, the presentation of information to the user or to any type of managing or monitoring entity may be performed personalized and in any of several ways including, by way of example, and not limitation, visual, acoustic, etc. For example, a button for sound (440) may be used to enable or disable the acoustic delivery of contextual or any other type of data/information (including by way of example without limitation, any kind of multimedia streaming and combinations thereof). This button may also be leveraged to enable or disable playing music or other encouraging sound in the background, or to trigger an out-loud-reader mechanism to read-out-loud contents on the display (e.g. text from a website, messages received from friends, etc.) when predetermined and/or selectable thresholds or levels on the user's velocity or general context are reached. Another button may be used to change the units of the gait characteristic being displayed (450), for example, velocity in meters per second, kilometers per hour, etc. In some embodiments, automatic localization or other means may be leveraged to infer the country of the user and automatically adapt units, language, and other variables. Additional buttons (460) may also be employed for other purposes, including but not limited to, displaying the gait characteristic in different format, or displaying different information, set preferences, modify any aspect or property of the presentation and/or any application, etc. and combinations thereof.

In a particular embodiment, the background of the display/screen in FIG. 4 (including the background of the chart (420)) may be set to a dark color (e.g. black) while the rest of elements (axes or grid of the chart (420), and elements (410), (430), (440), (450), (460)) are set to light colors. Any other settings, modifications, and combinations thereof are also possible. In some embodiments, any of the elements in FIG. 4 and/or any of their sub-elements and/or any additional elements not described herein may be optional (e.g. may or may not be displayed) and/or may be set and/or modified and/or organized in any other way, including combinations thereof, and/or any feature or any other property about any or all of them may be set or modified in any fashion, including combinations thereof.

Figure 5A:
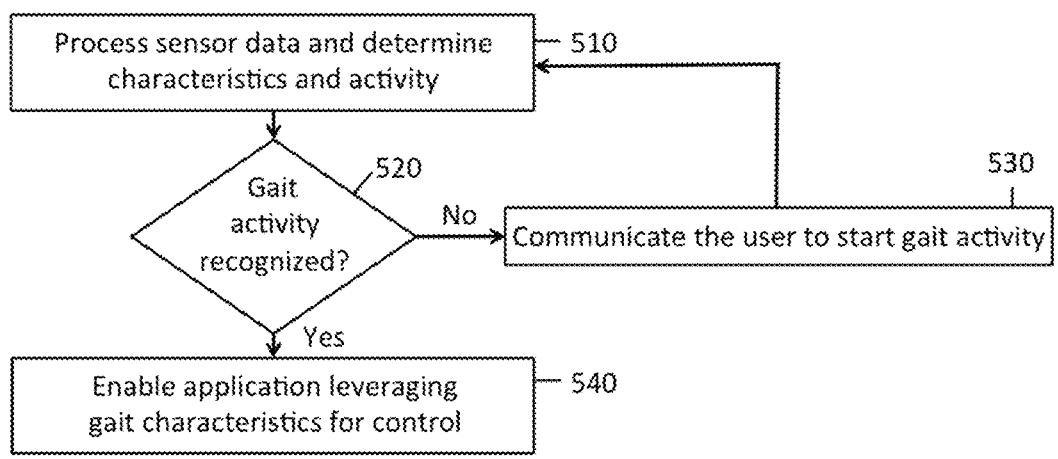
FIG. 5A presents a process flow diagram of an embodiment enabling and controlling an application with the user's gait characteristics.

FIG. 5A represents a flow diagram of possible basic steps of some embodiments enabling and controlling an application with the user's gait characteristics (including cadence). Initially, sensor data is processed to determine gait characteristics and activity (510); in some embodiments, only an accelerometer (tri-axial or any other type) embedded in the user's device may be used as sensor to determine the referred information, while other embodiments may employ additionally and/or independently any other type of sensor(s), device(s), sensor(s) embedded in other device(s), and/or any modifications and/or combinations thereof; by way of example without limitation, a tri-axial accelerometer in combination with GPS, or in combination with GPS and/or any other sensor (e.g. gyroscope, magnetometer, pressure sensor, etc.), or GPS on its own, or accelerometer and gyroscope on their own, or any radio-frequency based technology or any other technology on its own or combined with any other type of sensor, etc., and/or any other technology and/or methodology and variations and/or combinations thereof may also be used for enhanced accuracy, calibration or any other reasons/purposes. In some embodiments, processing of the sensor data may enable the determination/recognition of certain motion/gait characteristics and/or activity; by way of example without limitation, processing of accelerometer data through the wavelet transform (further details are provided with the description of FIG. 6) or any other methodology and/or combinations thereof may enable the determination of power, energy, frequency components, any kinematic parameter (e.g. user's velocity), peaks distribution over time, patterns, any statistics, etc., combinations thereof, or any other type of characteristic/information or any other data or parameter/metric that may or not be in any way related with any characteristic/activity/information, etc., and any or all of those data, metrics, parameters, and/or characteristics, etc. may be leveraged in any fashion to determine/recognize activity. In other embodiments, any other configuration, methodology, modification and/or combinations thereof may be employed; by way of example without limitation, some embodiments may use any type of technique/methodology (e.g. any type of machine learning technique with training data gathered in any fashion) to recognize activity independently of any other motion characteristic (which may also be determined with any methodology independently, in parallel, in combination, or in any other way regarding activity recognition), while other embodiments may employ any other methodology, tools, resources, techniques and/or mixtures and/or variations, modifications and/or combinations thereof.

In some embodiments, the gait/motion parameters or characteristics that may be determined/calculated/estimated/ inferred include, by way of example without limitation, speed, stride length, cadence, total distance, pace, gait efficiency, energy, power, changes in acceleration, speed variability, strike time, steps, and any combination thereof. In some embodiments, any number of gait/motion parameters and/or any other information may be leveraged to determine additional gait/motion parameters in any way; by way of example without limitation, physics principles may be used to determine distance (e.g. stride length) from velocity, and other parameters or characteristics that may be obtained in this or other fashion include energy consumption, different types of costs, etc. In some embodiments, any variations of any said characteristics or parameters and/or combinations thereof may also be determined in any fashion, and any user's characteristic such as height, weight, gender, age, etc. may also be used to help in the determination of the motion or gait parameters.

Some embodiments may test if the user is performing any type of gait activity (520), leveraging any of the characteristics/data/methodologies herein mentioned, or through any other methodology; in some embodiments, the type of user's movement that the system tries to recognize in (520) may include any activity that may be classified as human gait, in other words, any gait activity, including, by way of example without limitation, any type of walking, jogging, running, sprinting, ascending or descending stairs, exercising on any apparatus such as stationary elliptical trainer or bicycle, and any variation and/or combination thereof regardless of forward/backward direction, flat/inclined surface, type of environment, etc. In some embodiments, any gesture or movement different from walking, jogging or running may not be considered as a gait activity. In other embodiments, the user's movement to be recognized by the system in (520) may include any type of movement and/or activity. By way of example without limitation, a particular embodiment may consider walking, jogging, or running as gait activity. Any other variation and/or combination may also be possible.

As a result of the test in (520), in case of affirmative answer, some embodiments may enable any application and the use of gait characteristics for control (540). By way of example without limitation, regarding (540), some embodiments may enable or proceed with the triggering, launching, initiation, continuation, pausing, displaying, controlling in any way, interrupting, terminating, or any other action or procedure or combinations thereof of any process, function, procedure, program, application, environment or any other entity or element and/or combinations thereof, while any or all of the user's gait characteristics (including cadence) may be leveraged to control any aspect, feature, condition, property or any other attribute of any said process(es) and/or element(s) in any way. In a particular example of embodiment, once the mobile or wearable device recognizes that the user is walking with, for example, a determined velocity, cadence and/or stride length, the device may enable and/or display a virtual environment like the one represented in FIG. 1C, where attributes of element ((110)) or any other element may be controlled by the user's gait characteristics (e.g. the user's velocity may control in any way the velocity of element ((110)), or the user's stride length may control in any way the power of element ((110)), or the user's cadence may control in any way the stability of element ((110)), or any other variations and/or combinations thereof).

In some embodiments, the determined user's gait parameters, variables, or characteristics may also control any type of avatar of any form (including human, animal, object, etc.), any virtual environment, any aspect or object or element of any virtual environment, etc. and combinations thereof. In some embodiments, a virtual environment may include, by way of example without limitation, a representation of any setting in which the user perceives himself/ herself to be and within which interaction takes place; in some embodiments, the representation may be three-dimensional; in some embodiments, the representation may have any number of dimensions, use any type of technology, presentation and/or projection methodology/means and combinations thereof. In some embodiments, a virtual environment may also refer to any computer-based simulated environment allowing for any number of users, where the environment and/or their rules may draw from any reality and/or fantasy worlds and/or combinations thereof. In some embodiments, other examples of virtual environments may include, without limitation, any type of games, computer conferencing, chat-rooms, shared spaces, virtual reality, augmented reality, multi-user chat systems, mixed reality environments, multi-user games, multi-user games with persistent storage features, multi-user interactive environments, immersive environments, collaborative virtual environments, any other form of virtual habitats, etc. and/or combinations thereof. By way of example without limitation, in a particular embodiment, a game object may be controlled by characteristics of the user's gait in any fashion; for instance, a player may increase or decrease the speed of a car (e.g. element (110) in FIG. 1C, or any of the cars in scene (250) from FIG. 2B) in a game by increasing or decreasing his/her actual walking speed. In some embodiments, the determined user's gait parameters/variables may also control any aspect/property of the device (including any type and/or aspect of user interface, settings, etc.), or may also control any initiating, launching, influencing/altering in any way or terminating a task, program, application, function, communication or any other type of element or event or procedure that may have any influence on the user's device and/or any other devices, elements, processes, applications, etc. associated/connected in any way with the user's device; any variations and/or combinations thereof are also possible. In some embodiments, irregularities in the user's gait may also be detected through the comparison of any gait characteristic with known regular values stored anywhere in any fashion, or by means of any other method, and be leveraged to control any of the aspects/objects/entities etc. previously mentioned in any fashion.

In some embodiments, if the answer to the test in (520) is negative, the user will be prompted, or communicated in any way (e.g. text, visual message, acoustic message, mechanical vibration, etc. and combinations thereof) about the need to start a gait activity (530) in order to enable the application, proceed to the next level, continue a process, etc. as described for (540). The system may continue processing sensor data determining motion characteristics and activity, and keep communicating the user to start gait activity until a gait activity is recognized. In some embodiments, the system may employ a predetermined time as a threshold (a value which may be constant or variable depending on user's context, choice, etc.), after which, if the user has not initiated a gait activity, the whole process/application/procedure or some aspect of it may be terminated and/or some element may be disabled. In other embodiments, any condition, event, action, etc. may be used to end this loop and terminate the whole process, continue to the next step in some way, or any other possibility depending on any reasons/circumstances and combinations thereof.

Figure 5B:
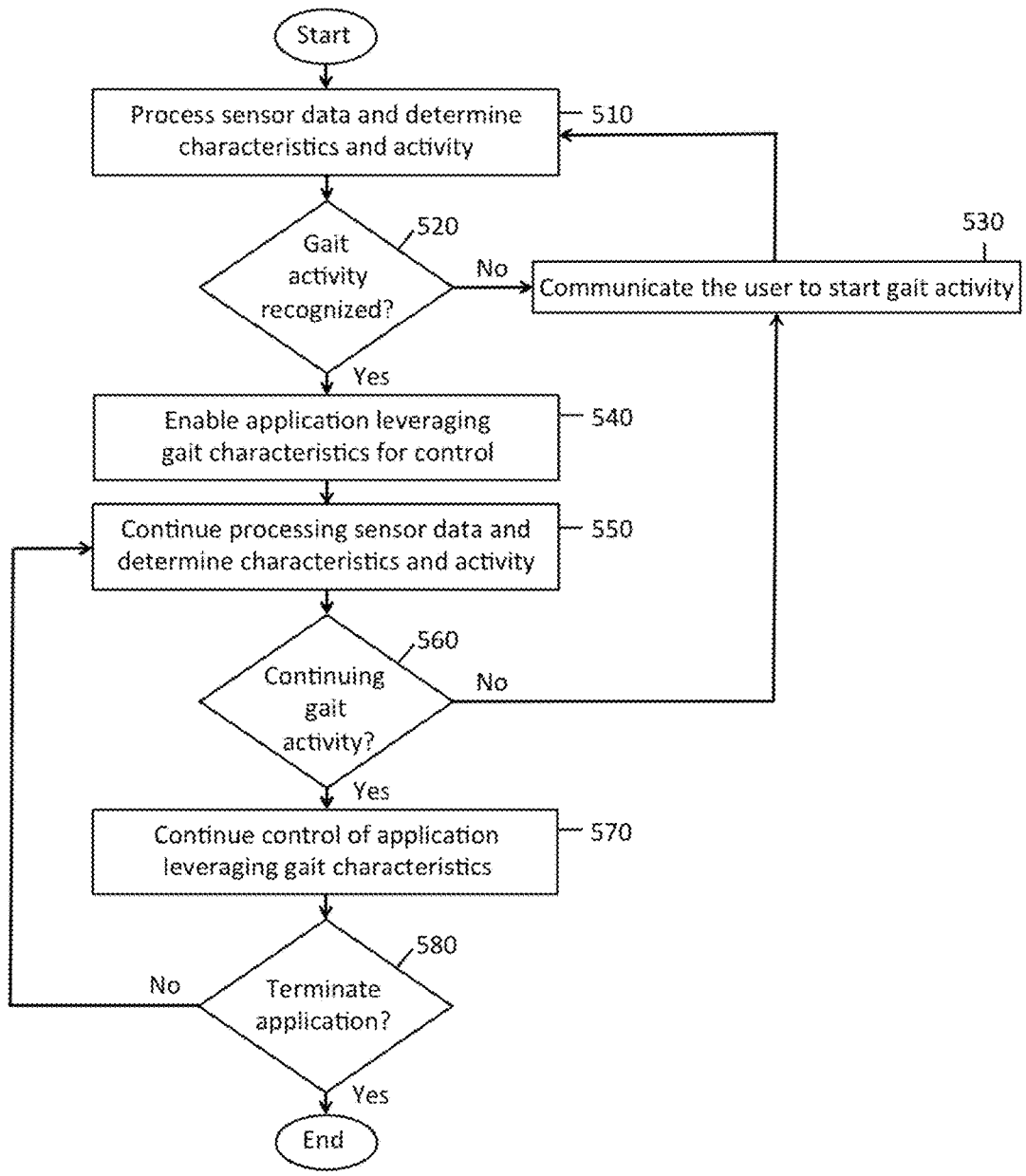
FIG. 5B presents a process flow diagram of another embodiment enabling and controlling an application with the user's gait characteristics.

FIG. 5B represents an extension of the flow diagram of possible basic steps from FIG. 5A that may be applicable to other embodiments. By way of example without limitation, as a result of the test in (520), in case of affirmative answer, following step (540), the device may be continuously processing sensor data and measuring or determining the user's gait characteristics and activity (550), in order to update the controlling characteristics and their controlled elements in any way (for example as described for (540)) with any change. This may be represented by step (570) in FIG. 5B, which is reached after affirmatively testing that gait activity is continuing (560). In case of a negative result from the test in (560), the system would communicate the user to start gait activity (530) and start the processing of sensor data to determine characteristics and activity (510) again. It is worth noting that in some embodiments, steps (550) and (510) may present differences, because step (550) may make use of some assumptions/knowledge of past states which may not be available for step (510) when the processing is started from scratch; consequently, step (550) may present some simplifications and/or advantages over step (510). In other embodiments, any differences may be avoided depending on any reasons/circumstances. In a similar way, it is worth noting that steps (540) and (570) may present some differences in some embodiments because of reasons similar to those noted for (550) and (510), while in other embodiments any differences may be avoided depending on any reasons/circumstances. It is also worth noting that in some embodiments, the controlling performed with the gait characteristics or in any other way may include the possibility of interrupting, pausing, terminating or in any other way modifying the influence or control of the user over any of the referred elements. By way of example without limitation, the device may disable or terminate the application (580), or the device may disable or terminate the displaying of any or all aspects or elements of the virtual environment represented in FIG. 1C or FIG. 2B when the user stops walking or when the user performs any action (e.g. press a button, perform some voice command, perform a certain movement, etc. and/or combinations thereof).

Some embodiments may allow any variations, modifications, additions, eliminations, etc. and/or combinations thereof.

Figure 6:
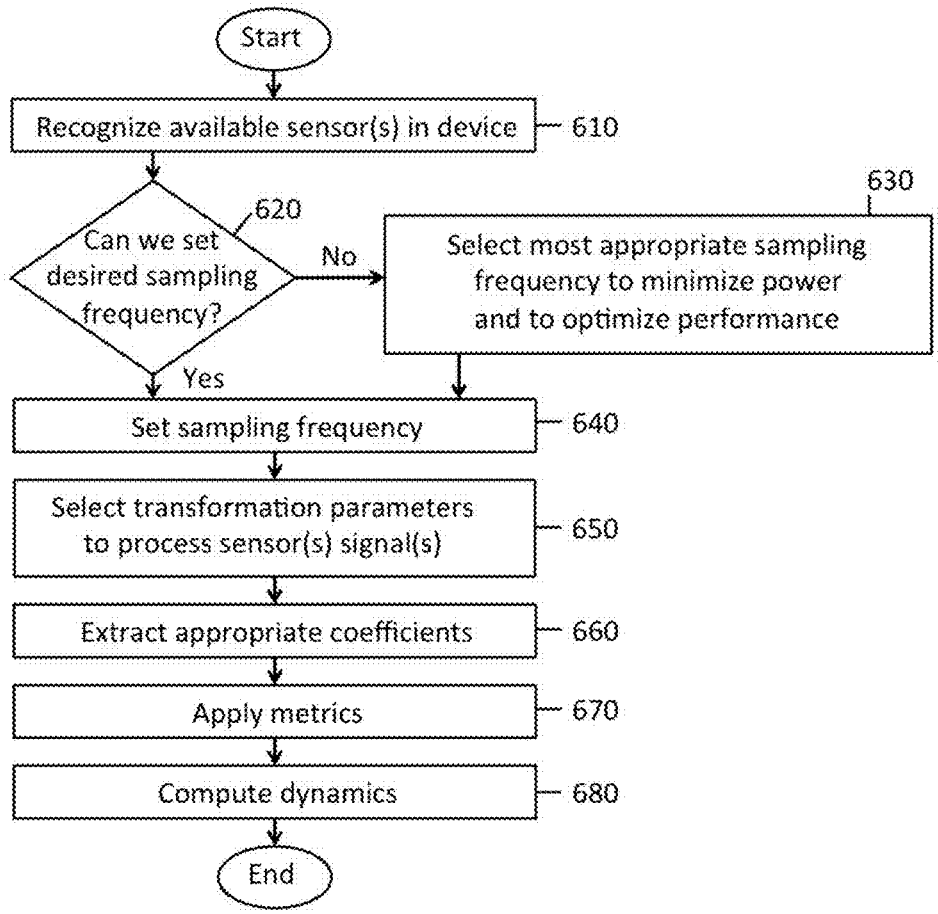
FIG. 6 illustrates a process flow diagram for the user's dynamics information determination according to one embodiment.

FIG. 6 illustrates a flow diagram of one embodiment with possible basic steps of a method for providing a user's dynamics information. The available sensors in the device are recognized in (610). Some embodiments may employ adaptable algorithms to be able to work with different types of devices (which may have, by way of example, and not limitation, different operating systems, different hardware features, different types of sensors, etc.). In some embodiments, the user's mobile device may have multiple sensors and sensor fusion techniques may be applied to enhance the solution. In other embodiments, the user's device may have very basic functionality and be equipped with a single accelerometer, and the algorithm will adapt to those devices to provide adequate results.

For the purpose of obtaining the dynamics of the user through the processing of sensor(s) signal(s), some embodiments may select an appropriate sampling frequency, which optimizes performance and attempts to minimize power consumption. In some embodiments, it may not be possible to set a desired sampling frequency (620). By way of example, and not limitation, some operating systems may allow the selection of predefined sampling frequency levels, which may work as indicators of the final sampling frequencies, but there is no guarantee of obtaining a specific frequency value. In fact, the final sampling frequency values may also be device and hardware specific. In conclusion, the algorithm in some embodiments will need to adapt to the available sampling frequencies in each particular device. In this sense, the sampling frequency may be selected (630) taking into account two criteria: first, performance optimization; second, power consumption minimization. In fact, optimum performance may depend on the sampling frequency among other factors. In some embodiments, the quality of the results obtained through the application of the wavelet transform to process the sensor(s) (e.g. accelerometer) signal(s) may depend on the sampling frequency. Once the desired or available sampling frequency has been selected, that frequency is set in the device (640). Some embodiments may use single axis sensor information to be processed (by way of example and not limitation, acceleration in x-axis, acceleration in y-axis, acceleration in z-axis). Some embodiments may use the signal vector module to be processed (by way of example and not limitation, the signal vector module of a tri-axial accelerometer). Some embodiments may use different configurations and/or combinations of sensors signals (including but not limited to sensor fusion information) to be processed. It must be noted that in some embodiments, the set frequency may still vary depending on a variety of factors, including but not limited to, device-specific behavior. Consequently, in some embodiments, a frequency resetting procedure may be necessary to maintain desired performance. Some embodiments may use dynamic selection of sampling frequency; by way of example and not limitation, when periods of inactivity are detected, the sampling frequency may be reduced in order to minimize power consumption, and once some activity is detected again, the sampling frequency may be increased again to deliver desired performance.

In some embodiments, the selection of the transformation parameters to process the sensor(s) signal(s) may take place after the sampling frequency is set (650). In some embodiments, the wavelet transform may be applied for processing sensor(s) signal(s). In other embodiments, other transformations may be applied, including but not limited to, short-time Fourier transform, other techniques leveraging Fourier analysis, application of filter banks, etc. In other embodiments different combinations of techniques, methodologies and transformations including wavelets maybe used. In some embodiments, the parameters of each transformation, which by way of example and not limitation, may comprise levels of decomposition, mother wavelet, processing time window parameters, etc. may be set appropriately/dynamically to optimize performance and minimize computation burden.

In some embodiments, the appropriate transformation coefficients may be obtained (660) and be leveraged in subsequent processes in combination with other parameters and metrics (670). In some embodiments, the application of metrics with the previously obtained information results in excellent correlations with the velocity of the user, and the activity of the user (e.g. walking, running, jumping, etc.), leading to a characterization of the user dynamics (680). In some embodiments, by way of example and not limitation, weighted (e.g. by levels, number of coefficients, etc.) energies of wavelet transform coefficients may provide an excellent indicator to directly choose the appropriate coefficients from which to obtain a reconstructed wave whose positive-to-negative transitions will mark each step of the user. For instance, the summation of the square of the wavelet transform detail coefficients, divided by the product of the number of detail coefficients at each decomposition level with the total number of decomposition levels plus one minus the actual decomposition level, provides a metric to classify the levels of decomposition; choosing the decomposition level with the highest value of said metric, and applying a reconstruction with its detail coefficients, delivers a wave whose positive-to-negative transitions will mark each step of the user. In some embodiments, useful metrics may comprise the summations of the square of transformation coefficients, these summations scaled by some factor (including but not limited to the number of coefficients, the number of levels of decomposition, a constant, etc.), or any other type of combinations. In some embodiments, the summations of weighted energies of transformation coefficients adequately scaled by some factor (including but not limited to level of decomposition) may provide an excellent correlation with the kinetic energy of the user. For instance, calling weighted energies for each decomposition level to the summation of the square of the wavelet transform detail coefficients, divided by the product of the number of detail coefficients at each decomposition level with the total number of decomposition levels plus one minus the actual decomposition level, and applying the square root to the summation of said weighted energies for each decomposition level being divided by the actual level, delivers an estimation of the velocity. In some embodiments, some of the coefficients may be avoided for the calculation of metrics, and appropriate combinations of summations of weighted energies may be leveraged to compute information comprising velocity. In some embodiments, criteria to avoid transformation coefficients in the calculation of metrics may comprise: selection of a threshold, frequency content, etc. Some embodiments may leverage statistics (including but not limited to, range, mean, skewness, standard deviation, etc.) of the energies of transformation coefficients, or any other features or combinations thereof to be combined with the previously mentioned computed kinematic information and obtain user dynamics information comprising activity. By way of example and not limitation, some embodiments may leverage as metrics the summations of descriptive statistics (or combinations of them) of energies of transformation coefficients of predetermined levels (choice criteria may comprise threshold, frequency content, etc.), in combination with other summations of descriptive statistics (or combinations of them) of energies of transformation coefficients of predetermined levels (choice criteria may again comprise threshold, frequency content, etc.), in combination with velocity information.

In some embodiments, an indication of the fundamental frequency or cadence of the gait of a mobile or wearable device user, may be determined through the analysis of a motion sensor signal (e.g. the motion sensor can be a tri-axial accelerometer embedded within the device), by means of a Fourier transformation of said signal over a time window. By way of example without limitation, choosing a time window of four seconds for the motion sensor signal, the Fourier transformation of said signal may provide a representation of its frequency components; in some cases, the strongest frequency component in said representation may coincide with the fundamental frequency of the user's gait or cadence; however, it must be noted that in some conditions, the analysis through the Fourier transformation may deliver misleading results, and special considerations may need to be taken into account to correct those results; by way of example without limitation, the combination of Fourier transformation with other techniques (e.g. wavelet transformation, Hilbert transformation, peak counting, correlation, autocorrelation, thresholding in time domain, and/or any other and/or combinations thereof) may help increase the accuracy in the determination of the user's cadence. By way of example without limitation, a cadence solution obtained through Fourier transformation analysis can be confirmed or rejected by a cadence solution obtained independently by any other technique (in case of rejection, priority can be given, for example, to the solution closest to the past (previous processing) cadence value); and in case of several techniques being used, a majority vote could be employed to decide on the final solution in case of discrepancies. Additional examples of combinations of techniques to obtain cadence are included in the rest of this specification.

In some embodiments, an indication of the fundamental frequency of a motion sensor signal (or an indication of the cadence of a mobile or wearable device user's gait) can be determined by means of an autocorrelation of the motion sensor signal over a time window. By way of example without limitation, selecting the motion sensor signal over a four seconds time window and performing an autocorrelation of said signal, delivers another signal (for clarity purposes, called second signal, which typically consists of a central maximum surrounded by secondary minima and maxima), from which the inverse of the time distance between the central maximum of said second signal and the largest secondary maximum of said second signal, represents an indication of the fundamental frequency of the original motion sensor signal over said four seconds time window. Some embodiments may use a different length of the time window (e.g. two seconds, twenty seconds, sixty seconds, or any other length based on criteria comprising computational costs, dynamism of the solution, accuracy of the solution, frequency content, update frequency, and/or any others). Some embodiments may use different approaches to obtain the previously called second signal, comprising by way of example without limitation, a further division of the signal by its variance, and/or using a pre-processing phase to filter the original motion sensor signal at a particular frequency band (e.g. using a dynamic filter whose central frequency is updated over time based on a previously determined fundamental frequency of the motion signal obtained by means of a frequency transformation; or using the wavelet transformation to filter the motion signal over a range of frequency bands, in response to an indication that the mobile device has experienced a substantial orientation change, wherein said indication is obtained through the analysis of the motion signal with the Fourier transformation), and/or pre-conditioning the original motion sensor signal with any type of filter in any way, and/or using a pre-processing phase to offset the original motion signal in any direction by any amount, and/or using a post-processing phase to perform any of the previously mentioned approaches to reverse some or all of those changes, or to amplify some or all of said changes, or for any other purposes; criteria to follow any of these approaches include: increased accuracy, optimization of computational costs, increased dynamism in the solution, or any other. In some embodiments, any of the mentioned and/or any other additional approaches/methods/techniques/elements/processes and/or any combinations thereof may be used during the pre-processing, post-processing, and in-processing stages, in any way, for any purposes, and according to any criteria.

In some embodiments, the motion sensor leveraged to obtain the user's gait cadence may be an accelerometer; in some embodiments, the motion sensor may be a single-axis accelerometer; in some embodiments, the motion sensor may be a triaxial accelerometer, and each one of the axis may be used independently; in other embodiments, the motion sensor may be a triaxial accelerometer embedded within the device, and the three axial components may be leveraged to obtain a signal vector module; in other embodiments, the motion sensor may be a triaxial accelerometer, and the three axial components may be leveraged to obtain different combinations of correlations, which may be processed to obtain the fundamental frequency of the motion of the device; by way of example without limitation, some embodiments may use the correlation between accelerations of x and y axis and/or the correlation between x and z axis, and/or the correlation between y and z axis, and analyze the resulting signals in the time domain (e.g. event detection by means of thresholding using a moving average of the signal as threshold) or in the frequency domain (e.g. leveraging Short Time Fourier Transform), or by means of any other approach or combinations thereof (e.g. leveraging the wavelet transformation to obtain both time and frequency information of the signal), or any other techniques and/or combinations thereof for any purposes.

In some embodiments, the motion sensor may be embedded within the device; in other embodiments, the motion sensor may be in a wearable unit independent from the mobile device, and positioned in any way and in any location; in some embodiments the motion sensor may be a gyroscope; in other embodiments the motion sensor may comprise an accelerometer (uni-axial or tria-axial) and/or a gyroscope (uni-axial or tria-axial) and/or a magnetometer (uni-axial or tria-axial) and any sensor fusion techniques (e.g. Kalman filtering, particle filtering, or any other) may be leveraged to increase the accuracy of the solution or for any other purposes; in other embodiments, any or all of the mentioned sensors (accelerometer and/or gyroscope and/or magnetometer) may be embedded within the mobile device, and/or independently positioned in any location by means of separate wearable units in any way. Some embodiments may use any combinations of any of the previously mentioned approaches, and/or aspects, and/or elements, and/or processes, and/or any other, in any fashion.

In some embodiments, the time window considered to process the motion sensor signal may be offset over time in any fashion as additional samples from said motion sensor keep arriving for processing. By way of example without limitation, a four seconds time window may overlap 50% with the next four seconds time window selected for the next processing; in other words, the last half of the first time window coincides with the first half of the second time window. In other embodiments, different lengths of time window and/or different overlapping factors and/or different approaches and/or combinations thereof may be used for the continuous processing of the motion sensor signal. In another example of embodiment, a four seconds time window may be selected to process the motion sensor signal every half a second, regardless of the motion sensor sampling frequency (downsampling, upsampling, filtering, and/or any other technique and/or combinations thereof may be leveraged to adapt to particular hardware and/or software conditions); in this example, the overlapping factor is larger than in the previous example, and the update frequency and dynamism (e.g. capability to quickly adapt to changes) of the solution have increased. In some embodiments, any possible overlapping factor, length of time window, update frequency, dynamism of the solution, and/or any other element/feature and/or combinations thereof may be selected. By way of example without limitation, a fixed length time window may be selected and said time window may be offset every time a new sample arrives from the motion sensor (accepting the new arriving sample and discarding the oldest sample from the fixed length time window (again, downsampling, upsampling, filtering, and/or any other technique and/or combinations thereof may be leveraged to adapt to particular hardware and/or software conditions, if needed)), in such a way that the update frequency of the solution may be equal to the sampling frequency of the motion sensor; in other words, we may obtain the fundamental frequency (or cadence) of a mobile device user with an update frequency equal to the motion sensor sampling rate; in some embodiments, by way of example without limitation, the device motion sensor sampling rate may be equal to 60 Hz, or 120 Hz, thus obtaining an update frequency for the user's cadence greater than the user's step frequency; this is an important aspect for certain applications requiring increased dynamism in the solution (for example to control an aspect of an application or to control a process in a mobile device with the user's cadence, with an update frequency greater than the user's step frequency, thus improving the user's experience over other approaches). In other embodiments, we may work with any other motion sensor sampling rates and leverage upsampling, downsampling, filtering or any other technique to obtain an update frequency for the user's cadence higher or lower than the user's step frequency.

In some embodiments, during the processing of the original motion sensor signal (e.g. signal from an accelerometer within the device) over a time window to determine the fundamental frequency (or cadence) using autocorrelation, a pre-processing phase may be included to filter said motion sensor signal in any fashion (e.g. filter as a result of a frequency analysis, e.g. Fourier analysis or any other, of said signal); by way of example without limitation, said signal may be applied a Fourier transformation from where the frequency components of said signal may be analyzed; in particular, focusing on the frequency components below a threshold of, for example, 0.5 Hz, and above 0 Hz, if these low frequency components are stronger than the rest of frequency components of the signal (e.g. their amplitudes in the Fourier transformation domain are larger than the amplitudes of the rest of frequency components of said Fourier transformation above 0.5 Hz), that may indicate a substantial orientation change experienced by the device.

The term substantial orientation change may be defined in some embodiments, by way of example without limitation, as any orientation change (in any number of dimensions) experienced by a mobile device that causes low frequency components other than those due to gravity (e.g. below a threshold of 0.5 Hz but larger than 0 Hz) of an accelerometer signal (the accelerometer being within said device), to have an amplitude (as observed, for example, through a Fourier transformation of said signal) larger than the rest of frequency components above the threshold of 0.5 Hz. In other embodiments, the threshold of 0.5 Hz to refer to low frequencies may be modified (made larger or smaller, but always keeping the sense of low frequencies in the context of gait analysis in which typical fundamental frequencies may approximately range from 1 Hz to 4 Hz), and the condition to be fulfilled by the amplitude of said low frequencies in comparison with the rest of frequencies may be relaxed (e.g. the maximum amplitude of said low frequencies may be above 80% (or 120% or any other figure that may depend on a plurality of criteria) of the maximum amplitude of any other frequency outside the low frequencies range); in some embodiments, different metrics/figures may be leveraged to refer to approximately the same term. By way of example without limitation, the term low frequencies may refer in some embodiments to the frequencies below the typical lower limits in the values of gait cadence (e.g. below 1 Hz) without considering frequencies due to gravity (typically 0 Hz); in some embodiments the upper threshold for low frequencies may be lower (e.g. below 0.5 Hz, or below 0.3 Hz, or any other value), and the term low frequencies may refer to any frequency that may allow the detection of a substantial orientation change experienced by the device, keeping the sense of low frequencies in the context of gait analysis in which typical fundamental frequencies may approximately range from 1 Hz to 4 Hz. In some embodiments, for example, if the upper threshold for low frequencies is very small (e.g. 0.3 Hz) and the Fourier transformation of the accelerometer signal offers low granularity in the selection of frequency components (e.g. there is only one low frequency component below said threshold and above 0 Hz), the detection of a substantial orientation change experienced by the device may comprise the comparison of the amplitude of that only low frequency with the amplitudes of the other frequency components obtained through the Fourier transformation. By way of example without limitation, frequency bands rather than setting thresholds may be used to refer to low frequencies or any other frequencies (e.g. in some embodiments, the low frequency amplitude(s) may be compared with a subset (e.g. a range of frequencies comprising the strongest amplitudes, or a range of frequencies comprising the previous values of cadence, or a range of frequencies comprised between certain thresholds, etc.) of the other frequency amplitudes); or energies of frequency components (either precise, specific frequency components or whole frequency bands or sub-bands, or any other) rather than amplitudes may be used; or any other possible modification and/or combination of any of the mentioned concepts/elements or any other may be used in other embodiments.

Substantial orientation changes may typically occur for example during movements and/or shakes performed by the user while carrying the device in his/her hand during a gait activity. In some embodiments, substantial orientation changes may refer to any type of orientation change experienced by the mobile or wearable device that distorts, and/or introduces noise in, and/or introduces artifacts in, and/or influences, and/or modifies the underlying information in the motion sensor signal about the gait movement, in any way. By way of example without limitation, said low frequency components due to a substantial orientation change may be strong enough to hide or distort or introduce noise or negatively influence or alter in any other way the underlying information relative to the original gait movement (e.g. the low frequency components may be so strong that an original fundamental frequency of e.g. 1.6 Hz may appear very weak (even negligible) in comparison with said low frequency components, to the extent that it could be interpreted that the fundamental frequency is now, for instance, 0.5 Hz instead of the real 1.6 Hz; any other type of distortions may also be considered. In cases of substantial orientation change, the original motion sensor signal may be filtered and/or processed in any fashion (e.g. by means of hardware and/or software) to mitigate and/or attenuate and/or counteract and/or influence in any way the distortion and/or noise and/or artifacts and/or influence and/or modification introduced by said substantial orientation change in the underlying gait information.

By way of example without limitation, as a result of a detection of a substantial orientation change, some embodiments may use a filter (e.g. high pass, or band pass) of any type (e.g. Butterworth, Chebyshev, or any other) or apply any type of pre-processing to try to eliminate the frequency components below 0.5 Hz (or any other threshold) from said motion sensor signal before being processed to determine the fundamental frequency. Taking into account the excellent qualities of wavelet transformation to, for instance, filter dynamic signals minimizing any extra distortion, we may apply a wavelet transformation to the original motion sensor signal (typical transformation parameters may be selected; by way of example without limitation: a mother wavelet from any of Haar, or Daubechies, or Coiflets, or discrete version of Meyer; and a number of levels of decomposition sufficient to account for the frequency bands we expect, which may depend on the number of signal samples we have, the length of the time window, or the sampling frequency; in a particular example, we may apply the wavelet transformation to the original motion signal using Haar mother wavelet and eight levels of decomposition); once the wavelet transformation coefficients are obtained, a wavelet reconstruction may be applied avoiding low frequency components/coefficients (getting rid of any other frequency component may also be possible and convenient in certain conditions); by way of example without limitation, the avoided low frequency components/coefficients may include those below the previously mentioned threshold of 0.5 Hz. In other words, we filter the original motion sensor signal leveraging a wavelet transformation by obtaining its wavelet transformation coefficients and applying a wavelet reconstruction avoiding coefficients corresponding to frequencies below 0.5 Hz; in this way, the wavelet reconstruction performed with all coefficients but those corresponding to low frequencies will be a filtered version of the original motion signal. Consequently, in this particular example, we are determining in real time the device user's cadence through the analysis of the motion sensor signal by means of a combination of techniques comprising: Fourier transformation (e.g. to analyze the frequency components of the motion sensor signal and decide if the signal needs to be filtered), wavelet transformation (to filter the signal), and autocorrelation of the filtered signal. In some embodiments, any modifications and/or combinations of any of the elements and/or processes and/or techniques mentioned and/or any other, may be applied in any fashion.

In some embodiments, abrupt changes in cadence (or motion sensor signal fundamental frequency) may be detected leveraging frequency and time information of the motion sensor signal. By way of example without limitation, abrupt changes in cadence may be characterized by sudden and/or fast (typically within a few seconds or even within fractions of a second) modifications in the value of said cadence; and wherein said abrupt modifications typically involve a relative change in the value of said cadence of at least 25% (e.g. a change from 2 Hz to 1.5 Hz involves a reduction of 25% relative to 2 Hz), although other values, larger and/or smaller, may also be considered. By way of example without limitation, abrupt changes in cadence may comprise: a change from 2 Hz to 1 Hz in the walking cadence of a mobile device user in a matter of 2 seconds, or a change from 2.1 Hz to 1.2 Hz in the walking cadence of a mobile device user in a matter of 2 steps, or a change from 0.8 Hz to 1.5 Hz in the walking cadence of a mobile device user in a matter of 3 steps, or a change from 1.9 Hz to 3.35 Hz in the gait cadence of a mobile device user in a matter of 1.5 seconds while he/she changes his/her gait from walking to running, or a change from 3.2 Hz to 1.8 Hz in the gait cadence of a mobile device user in a matter of 3.5 seconds while he/she changes his/her gait from running to walking, or any other possible combinations reflecting an important change in the value of the cadence (e.g. a factor of approximately 2 or less or more when the cadence is increased, and/or a factor of approximately 0.5 or less or more when the cadence is decreased) performed in a short period of time (typically within a few seconds).

Traditional approaches to determine cadence may fail when facing abrupt changes in cadence, because their processing of the motion signal may assume, for instance, a predetermined minimum time length of the user's step, or a predetermined frequency range of the user's cadence; the problem may be specially important when the abrupt changes in cadence (e.g. from 1 Hz to 2 Hz) result in the new cadence value (2 Hz) occupying some harmonic frequency of the previous values of cadence (1 Hz), in such a way that traditional methods may think of the new cadence value (2 Hz) as an harmonic of the previous cadence value (1 Hz), and find a subharmonic (½) of the new cadence (2 Hz) to be considered as the real cadence because it matches previous cadence values (1 Hz); consequently, traditional approaches would keep wrongly tracking said subharmonic as the fundamental frequency. Other examples may comprise any possible combinations and/or modifications of any of the concepts (including harmonics, subharmonics, and their orders) and/or figures and/or elements of the previous examples. It is worth noting that the problems may also arise with changes in cadence not necessarily involving integer multiples and/or submultiples of the original fundamental frequency.

In some embodiments, abrupt changes in the device user's cadence may be detected leveraging frequency and time information of the motion sensor signal (e.g. accelerometer signal, wherein said accelerometer is within the device). By way of example without limitation, we consider a mobile or wearable device user walking, and transitioning his/her cadence from 0.5 Hz to 1 Hz (other examples of embodiments may use different cadence values), whereby the device comprises a triaxial accelerometer with a sampling frequency of 50 Hz; the new value of 1 Hz for cadence has been determined (810) using e.g. any of the approaches described in this specification, but the new value is suspicious of being an error, because of the abrupt change in cadence (820). Consequently, there is a need to confirm as genuine the new cadence value, or reject it because it may be considered that the newly determined cadence is an error caused by harmonics of the previous cadence value (0.5 Hz). In other words, there is a need to detect genuine abrupt changes in cadence, and thus confirm as genuine the newly determined value of cadence. For this, a process composed of several stages will be explained next.

First, a pre-processing stage may comprise the identification of the accelerometer axis whose mean has the highest absolute value among the three axes, and/or the identification of two of the accelerometer axes whose means have the lowest absolute value among the three axes (830) (e.g. we identify the three axes of the accelerometer X, Y, and Z, and obtain the mean in the time domain for each one of them over a time window of, for example, four seconds; we obtain the absolute value of said obtained means, and compare them to identify the two accelerometer axes with the lowest means in absolute value; other embodiments may use any other length of time window or any other modifications according to criteria comprising: computing and/or storing costs and/or any other; other embodiments may use any other approaches and/or modifications and/or combinations thereof).

Once the two axes with the lowest means in absolute value have been identified (e.g. axes X and Y), an indication of a metric accounting for the average frequency value of the main (strongest) frequency components recorded over a pre-determined time window may be obtained for each of said two axes (840); for instance, said metric may be computed over a time window comprising the past twenty seconds; in some embodiments, different lengths of time window may be used (larger or shorter depending on criteria comprising accuracy, computing and storing costs, etc.), or different variables may be used for continuous updating of said metric with every new measurement/sample/processing obtained from the accelerometer signal, in such a way that there is no need to keep a window of past values; in other embodiments, different metrics may be used; for example, probabilistic models can be used to obtain a metric accounting for the strength/power and/or frequency value of each main frequency component recorded and the length of time during which said component was active; in other embodiments the metric may account for the frequency value of said component and the amount of time said value has been active over a length of time; other embodiments may use any combinations of any of said elements and/or concepts and/or any others in any fashion. For clarity purposes, we can call said determined indications X_probabl_freq and Y_probabl_freq (for X and Y axes respectively); in some embodiments, said determined indications may be retrieved leveraging any of the previously described approaches and/or using small databases, and/or registers, and/or look-up tables, and/or any kind of variables recording continuous updates in an application.

After determining said indications X_probabl_freq and Y_probabl_freq, the two previously identified axes (e.g. axes X and Y), are classified according to said indications (850); for example, if axis X has a value of said determined indication larger than axis Y, we can call axis X as primary axis and axis Y as secondary axis. Next, to check if there has been a genuine abrupt transition in the fundamental frequency, we focus (860) on a range of frequencies around the previously determined fundamental frequency (0.5 Hz), and we check if the current strength of the so called primary axis in a frequency band around the previously determined fundamental frequency is at least a threshold below the current strength of the so called secondary axis in the same frequency band (870); this strength comparison can be performed in terms of energy (e.g. using energy of a frequency component or energy of a frequency band, which can be determined for example leveraging a Fourier transformation or a wavelet transformation), or in terms of amplitude (e.g. using amplitude of a frequency component which can be determined for example through a Fourier transformation), or in terms of any other concept and/or element and/or any combinations thereof. Regarding the threshold for the strength comparison, recommended values for increased accuracy may be, by way of example without limitation: the larger quantity should be at least 2.25 times the smaller quantity if the comparison is made in terms of energies, or the larger quantity should be at least 1.5 times the smaller quantity if the comparison is made in terms of amplitudes; in some embodiments, different values (larger or smaller) may be used to account for particular conditions that may recommend tightening or relaxing said threshold. In some embodiments, any variations of any figures/concepts/approaches and/or any other and/or combinations thereof may be used.

In affirmative case regarding the previously referred strength comparison, we retrieve a history (880), over a pre-determined length of time right before the current time, of the values of the energies of both primary and secondary axes in the frequency band around the previously determined fundamental frequency (0.5 Hz); in some embodiments, said history of the values of the energies of both axes may span over several seconds (e.g. 10 seconds, although other values may also be possible depending on criteria comprising computing costs, storage costs, sampling frequency and/or any other), and it should be large enough to be able to register the transition. In some embodiments, instead of energies, the history of values may be of amplitudes of frequency components, obtained, for example, through the Fourier transform. In other embodiments, other approaches and/or figures and/or techniques and/or combinations thereof may be used.

Next, calling oldest_time_instant the instant of time corresponding to the oldest value registered in the previously mentioned history of values of strength (for clarity, it is worth remembering that strength can be expressed in terms of energy or amplitude or any other depending on the chosen approach), we check if the following three conditions are fulfilled: 1) the strength of the so called secondary axis over said frequency band at said oldest_time_instant is at least a threshold below the strength of the so called primary axis over the same frequency band at the same oldest_time_instant (881), and 2) the current strength of the so called primary axis in said frequency band is at least a threshold below the average strength of the primary axis in the same frequency band over the span of said history of values of strength (882), and 3) the current strength of the so called secondary axis in said frequency band is at least a threshold above the average strength of the secondary axis in the same frequency band over the span of said history of values of strength (883); if said three conditions are fulfilled, then some embodiments may consider that an abrupt transition in cadence has been detected (890), and consequently, the most recently determined fundamental frequency (1 Hz) is verified as genuine (891); otherwise, it would have been rejected (892) and some embodiments may use said rejection to try to keep tracking the old cadence values of 0.5 Hz (e.g. leveraging an adaptive filter centered at the old cadence values to emphasize them and reject what could be considered as errors due to harmonics, or with any other approach). Again, as previously described, regarding the threshold for the strength comparison, recommended values for increased accuracy may be, by way of example without limitation: the larger quantity should be at least 2.25 times the smaller quantity if the comparison is made in terms of energies, or the larger quantity should be at least 1.5 times the smaller quantity if the comparison is made in terms of amplitudes; in some embodiments, different values (larger or smaller) may be used to account for particular conditions that may recommend tightening or relaxing said threshold. In some embodiments, any variations of any figures/concepts/approaches and/or any other and/or combinations thereof may be used.

In some embodiments, a combination of time domain techniques and frequency domain techniques (e.g. Fourier transformation) may be used to detect abrupt changes in cadence; in other embodiments, techniques providing both time and frequency information (e.g. wavelet transformation) may be used; in other embodiments, combinations of any of those techniques and/or any other may be leveraged to obtain the time and frequency information to allow detection of abrupt changes in cadence. In other embodiments, any other modification and/or combination of any element and/or approach and/or technique and/or figure and/or combinations thereof may be used.

Some embodiments may leverage the previously mentioned information about the user's steps in combination with other metrics to enhance user's dynamics information, comprising velocity and activity. It is worth noting that in some embodiments, the user's cadence may be considered as the user's step frequency (inverse of the user's step time period). Some embodiments may leverage the obtained information on user's steps in combination with the information on user's dynamics to determine stride length. By way of example without limitation, using the physics principle velocity equals distance over time, once we have determined velocity, we can obtain distance (e.g. stride or step length) by using the time of each stride or step (step frequency equals inverse of the user's step time period). Some embodiments may leverage the information on user's dynamics to compute distance. Some embodiments may enhance distance through the combination of user's dynamics information with localization information. Some embodiments may use different techniques, principles and/or methodologies to obtain all the previous information and metrics, including but not limited to machine learning. In some embodiments, all the computation, processing, information presentation, and other steps may be carried out within a single mobile device without the need of external resources. In some embodiments, the computation or some other step or combinations of steps may be performed external to the mobile device, or with the assistance of some external element, such as external sensor, server, database or any other element. In some embodiments, software may be stored on the mobile or wearable device, for instance, in its memory for execution by its processor or processors. Some embodiments may store data structures and code on computer readable storage medium, which by way of example, and not limitation, may comprise field-programmable gate arrays, application-specific integrated circuits, magnetic and/or optical storage devices, etc.

In some embodiments, the sensor portion of the device or the device itself or any other device containing a sensor and with the capability to communicate in any fashion with the user's device, or any other type of device or accessory may be positioned or attached to any part of the user, including by way of example without limitation, the wrist, arm, hand, face, head, waist, chest, pocket, hat, shoe, any type of clothing, accessories and any combinations thereof and in any way. In some embodiments, the system may be trained to recognize and/or learn activity, motion type, attachment position of the device, movement characteristic, etc. In some embodiments, analysis of acceleration signature may help determine activity, motion type, attachment position of the device, movement/gait characteristic, etc. By way of example without limitation, the acceleration signal may be processed to identify maximums, minimums, mean, standard deviation, frequency components, period, orientation, distribution of peaks, patterns, etc. and/or combinations thereof in order to help determine activity, motion type, attachment position of the device, movement/gait characteristic, etc. In some embodiments, Fourier analysis, any kind of filtering, peak counting, determination of frequency components leveraging the wavelet transform or any other method and combinations thereof may also be utilized to determine user's gait activity, characteristics, etc. In some embodiments, any type of prompt to the user may also be leveraged to request information about his/her activity, motion type, attachment position of the device, movement/ gait characteristic, etc. In some embodiments, activity, motion type, attachment position, movement/gait characteristic, etc. may be determined through correlation of any type of sensor values or any type of parameter or metric generated with them, based on any type of model that has been calibrated in any fashion for a particular activity, motion type, attachment position, movement characteristic, etc. In some embodiments, any other sources, means, methods and/or configurations may be leveraged to determine activity, motion type, attachment position, movement/gait characteristic, etc., including by way of example without limitation, the use of sensors and/or signals obtained independently of the sensed acceleration (e.g. GPS), the use of statistics and/or any other empirical information, algorithms, databases or other information stored anywhere and in any fashion, combinations thereof, etc. In some embodiments, the referred methods, configurations, systems, etc. may be modified, updated and/or calibrated in any way, periodically or continuously over any time interval.

Some embodiments may include any external sources to obtain any parameter or information about movement, environment, context, etc. including by way of example without limitation, speed and/or distance monitors, any number of portable electronic devices (e.g. GPS receivers, any kind of computing and/or communications device, etc.), databases and/or networks. In some embodiments, other types of inputs may also be utilized, including by way of example without limitation, buttons, keys, keyboards, keypads, touchpads, joysticks, etc., which may be used in any fashion. Any type of satellite based navigation systems, cellular communications networks and other systems/networks may also be used to obtain speed in some embodiments (and/or provide feedback to help correct errors) under certain conditions.

In some embodiments, additional inputs may include traces from touch-sensitive screens, button presses, gesture recognition, voice commands, switches, and/or any other type of technological, physical or any nature means that allow the user to interact, and combinations thereof. In some embodiments, in addition to using gait characteristic for control, further control may be performed through any additional movements that the user may perform with the device, such as any type of tilting or any kind of gestures, including by way of example without limitation, any kind of raise, swing, twist, touch, press, swipe, drag, double touch, pinch, etc., and combinations thereof, regardless of performing them with or without direct contact to the device screen or any other element (e.g. the user may perform the pinch gesture touching a screen or in the air without touching a solid element). In some embodiments, any type of method may be employed to distinguish between different types of gestures, swings, twists, etc. that the user makes while he/she performs a pedestrian activity (e.g. walk, jog, run, etc.); by way of example without limitation, frequency analysis, filtering, acceleration thresholding, analysis of projection of gravity vector, feedback from other sensors, or any other technique/method and combinations thereof may be employed.

In some embodiments, the acceleration sensor may be an electrostatic or capacitance-coupling type, or any other technology (e.g. piezoelectric or piezoresistance type) now existing or later developed, and may be configured to deliver three-axis, two-axis, or one-axis acceleration. In some embodiments, in addition to accelerometers, any other type of technologies and/or sensors such as gyroscopes, magnetometers, pressure sensors, cameras, GPS, etc. may be used in any way to enhance accuracy or for any other purposes. In some embodiments, the user may have any number of any type of sensors, sensor units, devices, or accessories located anywhere in any fashion to determine the characteristics of his/her movement and/or for control or any other purposes.

In some embodiments, any processing, detection, recognition, or any other actions or operations may be performed regardless of the mode, state or any other condition of the device, application or any other entity, process or element. In other embodiments, any number of conditions and/or criteria of any type must be satisfied before proceeding with any of said actions or operations.

Any of the embodiments herein described may be implemented in numerous ways, including as a method, an apparatus, a device, a system, a computer readable medium, etc., and also be applicable in any environment, application (game, non-game, etc.), condition, etc. regardless of number of users, physical proximity, communication means, device, or any other factor.

Other configurations are also possible. By way of example, and not limitation, in some embodiments, all or part of the processes may be performed by chip-level systems, third-party applications, operating system kernel, firmware, or any other combination of hardware and/or software. In some embodiments, the software may be delivered in a variety of forms, including but not limited to, as stand-alone application, as library, as application programming interface, etc. In general, the functions of particular embodiments may be achieved by any means as is known in the art. Some embodiments may use distributed, networked sensors and/or systems, components, servers, databases, and/or circuits, and/or any combination of additional hardware and/or software and/or processing techniques and methodologies. Some embodiments may use any other type of sensor and/or system.

In some embodiments, sensors may be any of several types including, by way of example, and not limitation, any type of device, transducer or any other type of apparatus which may measure some quantity; in some embodiments, sensors may be implemented in any size, with any type of technique and technology, including but not limited to electronic, microelectronic, nanoelectronic, etc. By way of example, and not limitation, sensors may comprise any type of accelerometer, magnetometer, gyroscope, pressure sensor, proximity sensor, etc. and any other type of device sensitive to radio-frequency, sound, ultrasound, light, etc. including but not limited to, GPS antennas and/or their sensitive elements, WiFi antennas and/or their sensitive elements, and any other type of radio-frequency technology antennas and/or their sensitive elements. In some embodiments, sensors are integrated within the mobile or wearable device. In some embodiments, sensors or other mobile or wearable devices may be distributed outside the main mobile or wearable device, and they may communicate with the main mobile or wearable device by any means. Communication or transfer of data may be wired, wireless, or by any other means. In some embodiments, the user or other entity may rearrange characteristics of the components, or other features or elements of the system and the system may automatically adjust to new settings or arrangements.

Figure 7:
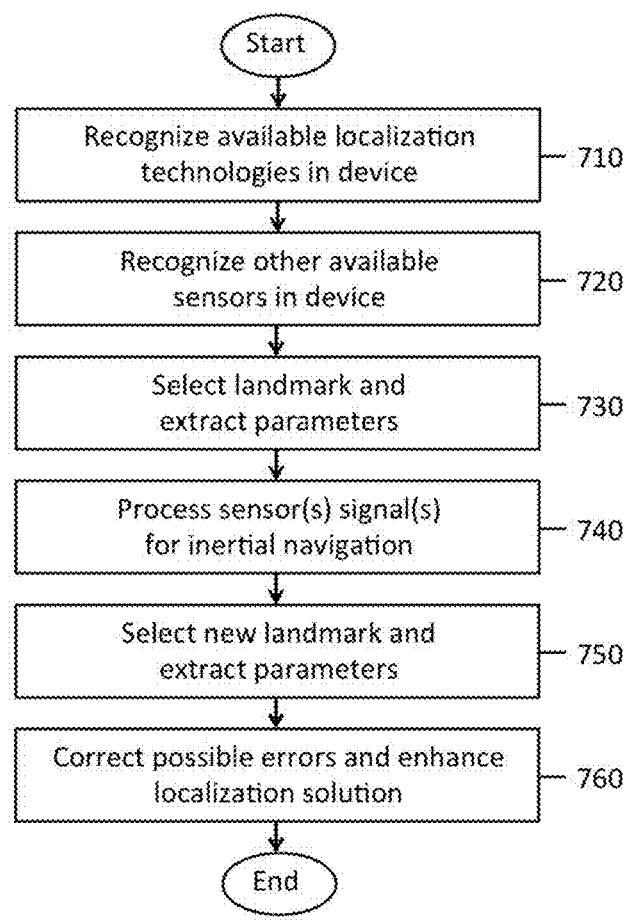
FIG. 7 illustrates a flow diagram for the process to enhance a user's dynamics and localization information according to one embodiment.
Figure 8:
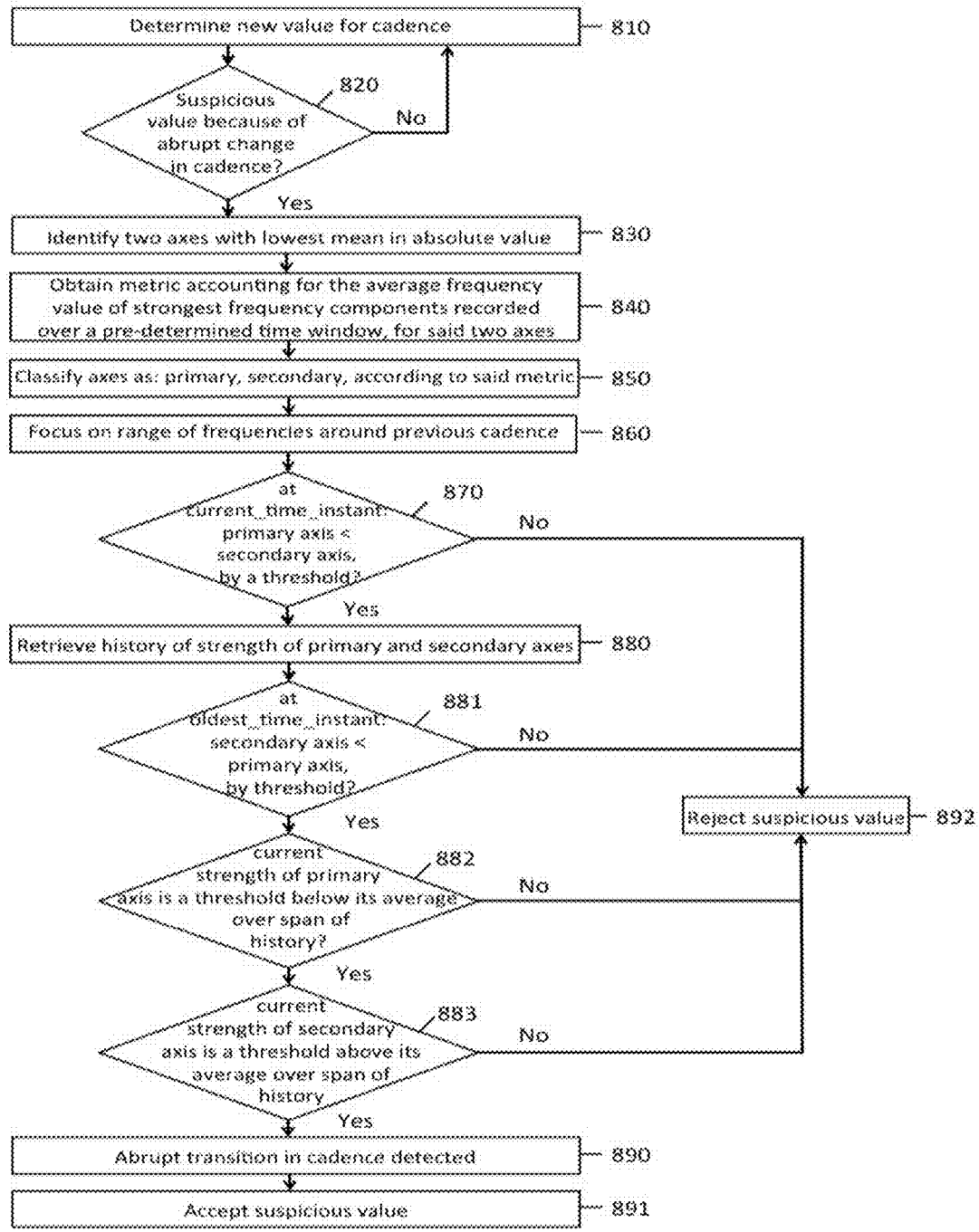
FIG. 8 illustrates a flow diagram for the process to detect an abrupt change in cadence according to one embodiment.

In some embodiments, a method for enhancing a user's dynamics and localization information may be used as shown in FIG. 7, which illustrates a flow diagram of possible basic steps. The available localization technologies are recognized in (710). By way of example and not limitation, localization technologies or methodologies may include satellite-based systems such as GPS, radio-frequency fingerprinting based techniques, and others based on various techniques, principles and/or technologies, including their combinations through a variety of methodologies such as Kalman filtering, particle filtering, etc. Regarding the radio-frequency fingerprinting based techniques, several technologies may be employed, including but not limited to, WiFi, cellular, Bluetooth, Zigbee, digital television, etc. In some embodiments, the use of satellite-based localization technologies may be avoided because the user may be located within buildings, urban canyons, or other environments in which the performance of these technologies is degraded. Even in those outdoor environments where the device may receive good quality signal from the satellites, these satellite-based systems may be avoided due to their high power consumption. In some embodiments, other localization techniques, technologies and methodologies may be used, including but not limited to, Near Field Communications, Ultra Wide Band, acoustic, ultrasound, any type of radio-frequency, etc. The available sensors in the device are recognized in (720). In some embodiments, these sensors may include accelerometer, magnetometer, gyroscope, pressure sensor, and others. In some embodiments, the device may include very basic functionality and the algorithm may need to adapt and perform efficiently with a single accelerometer. In other embodiments, the sensors in the device may include more than a single accelerometer, and sensor fusion techniques may be used. In other embodiments, other configurations of sensors may be possible.

In some embodiments, recognizable places may be set as landmarks from which to extract very precise features regarding their location and general context (730). By way of example and not limitation, Radio Frequency Identification, Bluetooth, Zigbee and/or other technologies and/or combinations of them may be leveraged using a variety of techniques to identify landmarks with a very high resolution. Leveraging the information on the user's dynamics, some embodiments may obtain accurate inertial navigation information (740). In some embodiments with basic functionality where the device may not be equipped with gyroscope and/or magnetometer, a variety of mechanisms to identify straight-line trajectories may be leveraged to adapt the inertial navigation solution. When a new identifiable landmark is reached, location and general context features are extracted (750). By way of example and not limitation, some embodiments may use GPS outdoors, or radio beacons indoors detected as peaks in signal strength within a radio-fingerprinting localization system, to identify landmarks. In other embodiments, the use of other types of beacons or landmarks, derived from a variety of technologies, that may use a variety of principles to obtain the required information, is also possible. This information may be leveraged using a variety of possible techniques and methodologies to correct possible errors on the user's dynamics and enhance the localization solution (760). Some embodiments may use manual calibration by the user introducing required calibration parameters in ways he/she may choose from a variety of techniques, technologies and methodologies. Other embodiments may use automatic calibration. In some embodiments, the calibration may be successfully applied to enhance both the information on localization and the user's dynamics and contextual information.

Some embodiments may use all the available information to identify the position (and transitions between positions) of the mobile device within the user's body; by way of example and not limitation, the position information may comprise: held in front in reading position, held in hand while walking, held in pocket while walking, etc. Some embodiments may use external elements comprising user's input to identify positions; in other embodiments, positions will be recognized internally by the mobile device leveraging sensors information.

Some embodiments may use any type of smartphones, mobile devices, wearable devices and/or sensors, or any other types of devices or combinations of them, including but not limited to, personal digital assistants, personal navigation systems, portable electronic devices, tablets, laptops, computers, and their peripheral devices. In some embodiments, the definition of mobile device may comprise any type of mobile phone, smartphone, wearable device and/or sensor, or any other types of device or wearable or combinations of them.

Some embodiments may use combinations of strategies and techniques, including, by way of example, and not limitation, machine learning techniques, probabilistic models, sensor fusion techniques, extraction of statistics, employment of filter banks, application of dimensionality reduction techniques, a variety of approaches for classification, etc. Details are omitted to improve the clarity of the description. In addition, some embodiments may use a variety of programming languages and methodologies in combination with varied hardware configurations and execution strategies.

Some embodiments may leverage context information and provide supplemental information, which may be obtained through any means and sources, including but not limited to, social networks. Particular embodiments may also be used for targeted advertising or targeted information based on context, enable shopping of any type of product or service which may or may not be related to the contextual information, etc.

In some embodiments, various applications may use the obtained information as a trigger for activation. Alternatively, a user may be able to set preferences for different applications depending on the obtained information. By way of example, and not limitation, a user may set the font size and other features of the content (also obtainable through internet or any other means) in his/her mobile device display according to his/her dynamics to improve the reading experience. By way of example, and not limitation, the user may or may not have ear-speakers or head-phones or any other appropriate hardware connected to his/her device and he/she may opt for triggering an out-loud-reader or other type of application to read-out-loud or in some other way adapt the presentation of the content in the device display when his/her dynamic information stays within some preselected threshold levels. By way of example, and not limitation, application(s) and/or service(s) may request, trigger or in some way enable advertising from a commercial ad server or any other type of server or entity using either velocity information, user dynamics, key words, or other criteria as advertising keys. In some embodiments, the user's velocity and other information, including advertisements, may be presented on the mobile and/or wearable device for consideration by the user. Again, depending on preferences and personal privacy policies, information and lists of acquaintances, either desired or undesired, may be presented to the user or to desired friends or other people.

Some embodiments may be used to enhance the location information and to identify points of maximum wireless signal strength, or points with no signal strength, enabling applications or services that effectively leverage that information. Applications of some embodiments may include route searching, planning and optimization, precise geo-tagging of photos, etc. By way of example and not limitation, personalized routing in maps using pedestrian velocity, may enhance features such as travel time estimation, places of interest, navigation, context-based search, etc. For example, a pedestrian walking from home to University may be more interested in sandwich shops rather than gas stations.

Applications of some embodiments may comprise monitoring a variety of information of people in a variety of circumstances or contexts, including but not limited to, health-care, army, sports, etc. Some embodiments may perform the monitoring in a remote way and/or extend the monitoring to animals, robots, machines, etc. In some embodiments, services may be provided through subscription. Some embodiments may be applied for the estimation of calories consumption, or the diagnosis of diseases, such as Parkinson's or other neurodegenerative diseases. Some embodiments may be applied for the identification and/or treatment of disorders, such as gait disorders, associated with a wide variety of conditions, including but not limited to neurologic and orthopedic conditions. Some embodiments may obtain a wide variety of user's information, including but not limited to velocity, activity, stride length, cadence, step count, gait patterns, distance, etc. Some embodiments may apply the information to help in the prevention of falls, accidents or any other undesirable events. Applications of some embodiments may also include contextual interactions, interactive games, augmented reality, and other types of services. By way of example, and not limitation, in games, the attacking and/or crashing strength or power of a user may be set proportional to his/her velocity and certain events or communications may be triggered based on context.

In some embodiments, the obtained information may be used for social networking applications, such as finding and/or establishing communication and/or sharing information with friends and/or other people and/or groups of people whose contextual information might or might not in some way be related. By way of example, and not limitation, in some embodiments, users may be able to share and see the real-time and/or historical contextual information of their friends, edit contextual information on maps, etc. In some embodiments, the observation of two or more mobile and/or wearable devices following similar contextual patterns, may lead to infer a friendship.

Some embodiments may also be applied to infer information from a wide range of biological or other types of sensors/signals, either from humans, animals, mechanical entities such as robots or other machines, etc. Other embodiments may also be applied to monitor and optimize a variety of processes, including but not limited to, industrial and managerial processes. Other embodiments may also have many more applications.

Although the foregoing text sets forth a detailed description of numerous different embodiments of the invention, it should be understood that the scope of the invention is defined by the words of the claims set forth at the end of this patent. The detailed description is to be construed as exemplary only and does not describe every possibly embodiment of the invention because describing every possible embodiment would be impractical, if not impossible. Numerous alternative embodiments could be implemented, using either current technology or technology developed after the filing date of this patent, which would still fall within the scope of the claims defining the invention.

Thus, many modifications and variations may be made in the techniques and structures described and illustrated herein without departing from the spirit and scope of the present invention. Accordingly, it should be understood that the methods and apparatus described herein are illustrative only and are not limiting upon the scope of the invention.

The invention claimed is:

1. A method comprising:
   determining a gait characteristic of a user of a mobile or wearable device in real time as the gait characteristic occurs; wherein the mobile or wearable device is carried by the user; and
   controlling an aspect of an application in the mobile or wearable device with the determined gait characteristic in real time as the gait characteristic occurs;
   wherein the determining the gait characteristic of the user comprises:
      detecting an orientation change, wherein the detecting leverages a comparison of at least a frequency amplitude obtained through a Fourier transformation of a motion sensor signal with other frequency amplitudes of said Fourier transformation; in response to the detecting, filtering said motion sensor signal leveraging a wavelet transformation.

2. The method of claim 1, wherein the gait characteristic of the user is a cadence of the user.

3. The method of claim 2, wherein the determining the gait characteristic is performed with an update frequency greater than the user's step frequency; and wherein the controlling the aspect of the application is performed with an update frequency greater than the user's step frequency.

4. The method of claim 2, wherein the controlling the aspect of the application comprises controlling an aspect of a virtual environment.

5. The method of claim 2, wherein the determining the gait characteristic leverages an accelerometer with three axes; and
   wherein the determining the gait characteristic further comprises:
   identifying two of the accelerometer axes whose means have lowest absolute values;
   determining for each one of the two identified axes an average of strongest frequency components;
   classifying the two identified axes by leveraging the determined for each one of the two identified axes average of strongest frequency components;
   comparing the two identified axes in terms of a current strength in a frequency band around a previously determined frequency; wherein the comparing leverages the classifying;
   retrieving a time history of values of the two identified axes, wherein the values are in the frequency band around the previously determined frequency;
   comparing the two identified axes in terms of a strength at an oldest time instant of the retrieved time history of values, wherein the values are in the frequency band around the previously determined frequency;
   comparing a current strength of a first of the two identified axes in said frequency band with an average strength of said first of the two identified axes in said frequency band; wherein said average strength of said first of the two identified axes is determined over the retrieved time history of values; and comparing a current strength of a second of the two identified axes in said frequency band with an average strength of said second of the two identified axes in said frequency band; wherein said average strength of said second of the two identified axes is determined over the retrieved time history of values.

6. The method of claim 5, wherein the determining the gait characteristic is performed with an update frequency greater than the user's step frequency; and wherein the controlling the aspect of the application is performed with an update frequency greater than the user's step frequency.

7. The method of claim 5, wherein the controlling the aspect of the application comprises controlling an aspect of a virtual environment.

8. The method of claim 7, wherein the determining the gait characteristic is performed with an update frequency greater than the user's step frequency; and wherein the controlling the aspect of the application is performed with an update frequency greater than the user's step frequency.

9. The method of claim 1, wherein the determining the gait characteristic is performed with an update frequency greater than the user's step frequency; and wherein the controlling the aspect of the application is performed with an update frequency greater than the user's step frequency.

10. The method of claim 1, wherein the controlling aspect of the application comprises controlling an aspect of a virtual environment.

11. The method of claim 1, wherein the determining the gait characteristic leverages an accelerometer with three axes; and wherein the determining the gait characteristic further comprises:
 identifying two of the accelerometer axes whose means have lowest absolute values;
 determining for each one of the two identified axes an average of strongest frequency components;
 classifying the two identified axes by leveraging the determined for each one of the two identified axes average of strongest frequency components;
 comparing the two identified axes in terms of a current strength in a frequency band around a previously determined frequency; wherein the comparing leverages the classifying;
 retrieving a time history of values of the two identified axes, wherein the values are in the frequency band around the previously determined frequency;
 comparing the two identified axes in terms of a strength at an oldest time instant of the retrieved time history of values, wherein the values are in the frequency band around the previously determined frequency;
 comparing a current strength of a first of the two identified axes in said frequency band with an average strength of said first of the two identified axes in said frequency band; wherein said average strength of said first of the two identified axes is determined over the retrieved time history of values; and
 comparing a current strength of a second of the two identified axes in said frequency band with an average strength of said second of the two identified axes in said frequency band; wherein said average strength of said second of the two identified axes is determined over the retrieved time history of values.

12. The method of claim 11, wherein the determining the gait characteristic is performed with an update frequency greater than the user's step frequency; and wherein the controlling the aspect of the application is performed with an update frequency greater than the user's step frequency.

13. The method of claim 11, wherein the controlling the aspect of the application comprises controlling an aspect of a virtual environment.

14. The method of claim 13, wherein the determining the gait characteristic is performed with an update frequency greater than the user's step frequency; and wherein the controlling the aspect of the application is performed with an update frequency greater than the user's step frequency.

15. A method comprising:
 determining a gait characteristic of a user of a mobile or wearable device in real time as the gait characteristic occurs; wherein the mobile or wearable device is carried by the user; and
 controlling an aspect of an application in the mobile or wearable device with the determined gait characteristic in real time as the gait characteristic occurs;
 wherein the determining the gait characteristic of the user comprises:
  determining a Fourier transformation of a motion sensor signal;
  comparing an amplitude of at least one frequency of said Fourier transformation with amplitudes of other frequencies of said Fourier transformation; wherein the at least one frequency is greater than 0 Hz and less than a threshold, and wherein the other frequencies are greater than the at least one frequency; wherein the threshold is greater than 0 Hz and less than 1 Hz;
  filtering the motion sensor signal leveraging a wavelet transformation; and applying an autocorrelation to the motion sensor signal after the filtering.

16. The method of claim 15, wherein the determining the gait characteristic is performed with an update frequency greater than the user's step frequency; and wherein the controlling the aspect of the application is performed with an update frequency greater than the user's step frequency.

17. The method of claim 15, wherein the controlling the aspect of the application comprises controlling an aspect of a virtual environment.

18. The method of claim 15, wherein the determining the gait characteristic leverages an accelerometer with three axes; and wherein the determining the gait characteristic further comprises:
 identifying two of the accelerometer axes whose means have lowest absolute values;
 determining for each one of the two identified axes an average of strongest frequency components;
 classifying the two identified axes by leveraging the determined for each one of the two identified axes average of strongest frequency components;
 comparing the two identified axes in terms of a current strength in a frequency band around a previously determined frequency; wherein the comparing leverages the classifying;
 retrieving a time history of values of the two identified axes, wherein the values are in the frequency band around the previously determined frequency;
 comparing the two identified axes in terms of a strength at an oldest time instant of the retrieved time history of values, wherein the values are in the frequency band around the previously determined frequency;
 comparing a current strength of a first of the two identified axes in said frequency band with an average strength of said first of the two identified axes in said frequency band; wherein said average strength of said first of the two identified axes is determined over the retrieved time history of values; and comparing a current strength of a second of the two identified axes in said frequency band with an average strength of said second of the two identified axes in said frequency band; wherein said average strength of said second of the two identified axes is determined over the retrieved time history of values.

19. The method of claim 18, wherein the determining the gait characteristic is performed with an update frequency greater than the user's step frequency; and wherein the controlling the aspect of the application is performed with an update frequency greater than the user's step frequency.

20. The method of claim 18, wherein the controlling the aspect of the application comprises controlling an aspect of a virtual environment.

21. The method of claim 20, wherein the determining the gait characteristic is performed with an update frequency greater than the user's step frequency; and wherein the controlling the aspect of the application is performed with an update frequency greater than the user's step frequency.

22. The method of claim 15, wherein the filtering leverages the threshold.

23. A method comprising:
determining a gait characteristic of a user of a mobile or wearable device in real time as the gait characteristic occurs; wherein the mobile or wearable device is carried by the user; and
controlling an aspect of an application in the mobile or wearable device with the determined gait characteristic in real time as the gait characteristic occurs;
wherein the determining the gait characteristic leverages an accelerometer with three axes; and wherein the determining the gait characteristic comprises:
identifying two of the accelerometer axes whose means have lowest absolute values; and
determining for each one of the two identified axes an average of strongest frequency components.

24. The method of claim 23, wherein the determining the gait characteristic is performed with an update frequency greater than the user's step frequency; and wherein the controlling the aspect of the application is performed with an update frequency greater than the user's step frequency.

25. The method of claim 23, wherein the controlling the aspect of the application comprises controlling an aspect of a virtual environment.

26. The method of claim 23, wherein the strongest frequency components are recorded over a time window.

27. The method of claim 23, wherein the determining the gait characteristic of the user further comprises: classifying the two identified axes by leveraging an indication determined for each one of the two identified axes; wherein the indication leverages the determined average of strongest frequency components.

28. The method of claim 23, wherein the determining the gait characteristic of the user further comprises: classifying the two identified axes by leveraging the determined for each one of the two identified axes average of strongest frequency components.

29. The method of claim 28, wherein the determining the gait characteristic of the user further comprises: comparing the two identified axes in terms of a current strength in a frequency band around a previously determined frequency; wherein the comparing leverages the classifying.

30. The method of claim 29, wherein the determining the gait characteristic of the user further comprises: retrieving a time history of values of the two identified axes, wherein the values are in the frequency band around the previously determined frequency.

31. The method of claim 30, wherein the determining the gait characteristic of the user further comprises:
comparing the two identified axes in terms of a strength at an oldest time instant of the retrieved time history of values, wherein the values are in the frequency band around the previously determined frequency.

32. The method of claim 31, wherein the determining the gait characteristic of the user further comprises:
comparing a current strength of a first of the two identified axes in said frequency band with an average strength of said first of the two identified axes in said frequency band;
wherein said average strength of said first of the two identified axes is determined over the retrieved time history of values.

33. The method of claim 32, wherein the determining the gait characteristic of the user further comprises:
comparing a current strength of a second of the two identified axes in said frequency band with an average strength of said second of the two identified axes in said frequency band; wherein said average strength of said second of the two identified axes is determined over the retrieved time history of values.

34. A system comprising:
one or more processors; and
a processor-readable medium including instructions which, when executed by the one or more processors, cause the one or more processors to perform functions comprising:
determining a gait characteristic of a user of a mobile or wearable device in real time as the gait characteristic occurs; wherein the mobile or wearable device is carried by the user; and
controlling an aspect of an application in the mobile or wearable device with the determined gait characteristic in real time as the gait characteristic occurs;
wherein the determining the gait characteristic of the user comprises:
detecting an orientation change, wherein the detecting leverages a comparison of at least a frequency amplitude obtained through a Fourier transformation of a motion sensor signal with other frequency amplitudes of said Fourier transformation; in response to the detecting, filtering said motion sensor signal leveraging a wavelet transformation.

35. The system of claim 34, wherein the gait characteristic of the user is a cadence of the user.

36. The system of claim 35, wherein the determining the gait characteristic is performed with an update frequency greater than the user's step frequency; and wherein the controlling the aspect of the application is performed with an update frequency greater than the user's step frequency.

37. The system of claim 35, wherein the controlling the aspect of the application comprises controlling an aspect of a virtual environment.

38. The system of claim 35, wherein the determining the gait characteristic leverages an accelerometer with three axes; and
wherein the determining the gait characteristic further comprises:
identifying two of the accelerometer axes whose means have lowest absolute values;
determining for each one of the two identified axes an average of strongest frequency components;
classifying the two identified axes by leveraging the determined for each one of the two identified axes average of strongest frequency components;

comparing the two identified axes in terms of a current strength in a frequency band around a previously determined frequency; wherein the comparing leverages the classifying;
retrieving a time history of values of the two identified axes, wherein the values are in the frequency band around the previously determined frequency;
comparing the two identified axes in terms of a strength at an oldest time instant of the retrieved time history of values, wherein the values are in the frequency band around the previously determined frequency;
comparing a current strength of a first of the two identified axes in said frequency band with an average strength of said first of the two identified axes in said frequency band; wherein said average strength of said first of the two identified axes is determined over the retrieved time history of values; and
comparing a current strength of a second of the two identified axes in said frequency band with an average strength of said second of the two identified axes in said frequency band; wherein said average strength of said second of the two identified axes is determined over the retrieved time history of values.

39. The system of claim 38, wherein the determining the gait characteristic is performed with an update frequency greater than the user's step frequency; and wherein the controlling the aspect of the application is performed with an update frequency greater than the user's step frequency.

40. The system of claim 38, wherein the controlling the aspect of the application comprises controlling an aspect of a virtual environment.

41. The system of claim 40, wherein the determining the gait characteristic is performed with an update frequency greater than the user's step frequency; and wherein the controlling the aspect of the application is performed with an update frequency greater than the user's step frequency.

42. The system of claim 34, wherein the determining the gait characteristic is performed with an update frequency greater than the user's step frequency; and wherein the controlling the aspect of the application is performed with an update frequency greater than the user's step frequency.

43. The system of claim 34, wherein the controlling the aspect of the application comprises controlling an aspect of a virtual environment.

44. The system of claim 34, wherein the determining the gait characteristic leverages an accelerometer with three axes; and wherein the determining the gait characteristic further comprises:
identifying two of the accelerometer axes whose means have lowest absolute values;
determining for each one of the two identified axes an average of strongest frequency components;
classifying the two identified axes by leveraging the determined for each one of the two identified axes average of strongest frequency components;
comparing the two identified axes in terms of a current strength in a frequency band around a previously determined frequency; wherein the comparing leverages the classifying;
retrieving a time history of values of the two identified axes, wherein the values are in the frequency band around the previously determined frequency;
comparing the two identified axes in terms of a strength at an oldest time instant of the retrieved time history of values, wherein the values are in the frequency band around the previously determined frequency;
comparing a current strength of a first of the two identified axes in said frequency band with an average strength of said first of the two identified axes in said frequency band; wherein said average strength of said first of the two identified axes is determined over the retrieved time history of values; and
comparing a current strength of a second of the two identified axes in said frequency band with an average strength of said second of the two identified axes in said frequency band; wherein said average strength of said second of the two identified axes is determined over the retrieved time history of values.

45. The system of claim 44, wherein the determining the gait characteristic is performed with an update frequency greater than the user's step frequency; and wherein the controlling the aspect of the application is performed with an update frequency greater than the user's step frequency.

46. The system of claim 44, wherein the controlling the aspect of the application comprises controlling an aspect of a virtual environment.

47. The system of claim 46, wherein the determining the gait characteristic is performed with an update frequency greater than the user's step frequency; and wherein the controlling the aspect of the application is performed with an update frequency greater than the user's step frequency.

48. A system comprising:
one or more processors; and
a processor-readable medium including instructions which, when executed by the one or more processors, cause the one or more processors to perform functions comprising:
determining a gait characteristic of a user of a mobile or wearable device in real time as the gait characteristic occurs; wherein the mobile or wearable device is carried by the user; and
controlling an aspect of an application in the mobile or wearable device with the determined gait characteristic in real time as the gait characteristic occurs;
wherein the determining the gait characteristic of the user comprises:
determining a Fourier transformation of a motion sensor signal;
comparing an amplitude of at least one frequency of said Fourier transformation with amplitudes of other frequencies of said Fourier transformation; wherein the at least one frequency is greater than 0 Hz and less than a threshold, and wherein the other frequencies are greater than the at least one frequency; wherein the threshold is greater than 0 Hz and less than 1 Hz;
filtering the motion sensor signal leveraging a wavelet transformation; and
applying an autocorrelation to the motion sensor signal after the filtering.

49. The system of claim 48, wherein the determining the gait characteristic is performed with an update frequency greater than the user's step frequency; and wherein the controlling the aspect of the application is performed with an update frequency greater than the user's step frequency.

50. The system of claim 48, wherein the controlling the aspect of the application comprises controlling an aspect of a virtual environment.

51. The system of claim 48, wherein the determining the gait characteristic leverages an accelerometer with three axes; and wherein the determining the gait characteristic further comprises:

identifying two of the accelerometer axes whose means have lowest absolute values;

determining for each one of the two identified axes an average of strongest frequency components;

classifying the two identified axes by leveraging the determined for each one of the two identified axes average of strongest frequency components;

comparing the two identified axes in terms of a current strength in a frequency band around a previously determined frequency; wherein the comparing leverages the classifying;

retrieving a time history of values of the two identified axes, wherein the values are in the frequency band around the previously determined frequency;

comparing the two identified axes in terms of a strength at an oldest time instant of the retrieved time history of values, wherein the values are in the frequency band around the previously determined frequency;

comparing a current strength of a first of the two identified axes in said frequency band with an average strength of said first of the two identified axes in said frequency band; wherein said average strength of said first of the two identified axes is determined over the retrieved time history of values; and comparing a current strength of a second of the two identified axes in said frequency band with an average strength of said second of the two identified axes in said frequency band; wherein said average strength of said second of the two identified axes is determined over the retrieved time history of values.

52. The system of claim 51, wherein the determining the gait characteristic is performed with an update frequency greater than the user's step frequency; and wherein the controlling the aspect of the application is performed with an update frequency greater than the user's step frequency.

53. The system of claim 51, wherein the controlling the aspect of the application comprises controlling an aspect of a virtual environment.

54. The system of claim 53, wherein the determining the gait characteristic is performed with an update frequency greater than the user's step frequency; and wherein the controlling the aspect of the application is performed with an update frequency greater than the user's step frequency.

55. The system of claim 48, wherein the filtering leverages the threshold.

56. A system comprising:
one or more processors; and
a processor-readable medium including instructions which, when executed by the one or more processors, cause the one or more processors to perform functions comprising:
determining a gait characteristic of the a user of a mobile or wearable device in real time as the gait characteristic occurs; wherein the mobile or wearable device is carried by the user; and
controlling an aspect of an application in the mobile or wearable device with the determined gait characteristic in real time as the gait characteristic occurs;
wherein the determining the gait characteristic leverages an accelerometer with three axes; and wherein the determining the gait characteristic comprises:
identifying two of the accelerometer axes whose means have lowest absolute values; and
determining for each one of the two identified axes an average of strongest frequency components.

57. The system of claim 56, wherein the determining the gait characteristic is performed with an update frequency greater than the user's step frequency; and wherein the controlling the aspect of the application is performed with an update frequency greater than the user's step frequency.

58. The system of claim 56, wherein the controlling the aspect of the application comprises controlling an aspect of a virtual environment.

59. The system of claim 56, wherein the strongest frequency components are recorded over a time window.

60. The system of claim 56, wherein the determining the gait characteristic of the user further comprises: classifying the two identified axes by leveraging an indication determined for each one of the two identified axes; wherein the indication leverages the determined average of strongest frequency components.

61. The system of claim 56, wherein the determining the gait characteristic of the user further comprises: classifying the two identified axes by leveraging the determined for each one of the two identified axes average of strongest frequency components.

62. The system of claim 61, wherein the determining the gait characteristic of the user further comprises: comparing the two identified axes in terms of a current strength in a frequency band around a previously determined frequency; wherein the comparing leverages the classifying.

63. The system of claim 62, wherein the determining the gait characteristic of the user further comprises: retrieving a time history of values of the two identified axes, wherein the values are in the frequency band around the previously determined frequency.

64. The system of claim 63, wherein the determining the gait characteristic of the user further comprises:
comparing the two identified axes in terms of a strength at an oldest time instant of the retrieved time history of values, wherein the values are in the frequency band around the previously determined frequency.

65. The system of claim 64, wherein the determining the gait characteristic of the user further comprises:
comparing a current strength of a first of the two identified axes in said frequency band with an average strength of said first of the two identified axes in said frequency band;
wherein said average strength of said first of the two identified axes is determined over the retrieved time history of values.

66. The system of claim 65, wherein the determining the gait characteristic of the user further comprises:
comparing a current strength of a second of the two identified axes in said frequency band with an average strength of said second of the two identified axes in said frequency band; wherein said average strength of said second of the two identified axes is determined over the retrieved time history of values.

67. A non-transitory processor-readable medium including instructions which, when executed by one or more processors, cause the one or more processors to perform functions comprising:
determining a gait characteristic of a user of a mobile or wearable device in real time as the gait characteristic occurs; wherein the mobile or wearable device is carried by the user; and
controlling an aspect of an application in the mobile or wearable device with the determined gait characteristic in real time as the gait characteristic occurs;
wherein the determining the gait characteristic of the user comprises:
detecting an orientation change, wherein the detecting leverages a comparison of at least a frequency amplitude obtained through a Fourier transformation of a motion sensor signal with other frequency amplitudes of said Fourier transformation; in response to the detecting, filtering said motion sensor signal leveraging a wavelet transformation.

68. The non-transitory processor-readable medium of claim 67, wherein the gait characteristic of the user is a cadence of the user.

69. The non-transitory processor-readable medium of claim 68, wherein the determining the gait characteristic is performed with an update frequency greater than the user's step frequency; and
wherein the controlling the aspect of the application is performed with an update frequency greater than the user's step frequency.

70. The non-transitory processor-readable medium of claim 68, wherein the controlling the aspect of the application comprises controlling an aspect of a virtual environment.

71. The non-transitory processor-readable medium of claim 68, wherein the determining the gait characteristic leverages an accelerometer with three axes; and wherein the determining the gait characteristic further comprises:
identifying two of the accelerometer axes whose means have lowest absolute values;
determining for each one of the two identified axes an average of strongest frequency components;
classifying the two identified axes by leveraging the determined for each one of the two identified axes average of strongest frequency components;
comparing the two identified axes in terms of a current strength in a frequency band around a previously determined frequency; wherein the comparing leverages the classifying;
retrieving a time history of values of the two identified axes, wherein the values are in the frequency band around the previously determined frequency;
comparing the two identified axes in terms of a strength at an oldest time instant of the retrieved time history of values, wherein the values are in the frequency band around the previously determined frequency;
comparing a current strength of a first of the two identified axes in said frequency band with an average strength of said first of the two identified axes in said frequency band; wherein said average strength of said first of the two identified axes is determined over the retrieved time history of values; and
comparing a current strength of a second of the two identified axes in said frequency bandwidth an average strength of said second of the two identified axes in said frequency band; wherein said average strength of said second of the two identified axes is determined over the retrieved time history of values.

72. The non-transitory processor-readable medium of claim 71, wherein the determining the gait characteristic is performed with an update frequency greater than the user's step frequency; and wherein the controlling the aspect of the application is performed with an update frequency greater than the user's step frequency.

73. The non-transitory processor-readable medium of claim 71, wherein the controlling the aspect of the application comprises controlling an aspect of a virtual environment.

74. The non-transitory processor-readable medium of claim 73, wherein the determining the gait characteristic is performed with an update frequency greater than the user's step frequency; and wherein the controlling the aspect of the application is performed with an update frequency greater than the user's step frequency.

75. The non-transitory processor-readable medium of claim 67, wherein the determining the gait characteristic is performed with an update frequency greater than the user's step frequency; and wherein the controlling the aspect of the application is performed with an update frequency greater than the user's step frequency.

76. The non-transitory processor-readable medium of claim 67, wherein the controlling the aspect of the application comprises controlling an aspect of a virtual environment.

77. The non-transitory processor-readable medium of claim 67, wherein the determining the gait characteristic leverages an accelerometer with three axes; and wherein the determining the gait characteristic further comprises:
identifying two of the accelerometer axes whose means have lowest absolute values;
determining for each one of the two identified axes an average of strongest frequency components;
classifying the two identified axes by leveraging the determined for each one of the two identified axes average of strongest frequency components;
comparing the two identified axes in terms of a current strength in a frequency band around a previously determined frequency; wherein the comparing leverages the classifying;
retrieving a time history of values of the two identified axes, wherein the values are in the frequency band around the previously determined frequency;
comparing the two identified axes in terms of a strength at an oldest time instant of the retrieved time history of values, wherein the values are in the frequency band around the previously determined frequency;
comparing a current strength of a first of the two identified axes in said frequency band with an average strength of said first of the two identified axes in said frequency band; wherein said average strength of said first of the two identified axes is determined over the retrieved time history of values; and
comparing a current strength of a second of the two identified axes in said frequency band with an average strength of said second of the two identified axes in said frequency band; wherein said average strength of said second of the two identified axes is determined over the retrieved time history of values.

78. The non-transitory processor-readable medium of claim 77, wherein the determining the gait characteristic is performed with an update frequency greater than the user's step frequency; and wherein the controlling the aspect of the application is performed with an update frequency greater than the user's step frequency.

79. The non-transitory processor-readable medium of claim 77, wherein the controlling the aspect of the application comprises controlling an aspect of a virtual environment.

80. The non-transitory processor-readable medium of claim 79, wherein the determining the gait characteristic is performed with an update frequency greater than the user's step frequency; and wherein the controlling the aspect of the application is performed with an update frequency greater than the user's step frequency.

81. A non-transitory processor-readable medium including instructions which, when executed by one or more processors, cause the one or more processors to perform functions comprising:

determining a gait characteristic of a user of a mobile or wearable device in real time as the gait characteristic occurs; wherein the mobile or wearable device is carried by the user; and controlling an aspect of an application in the mobile or wearable device with the determined gait characteristic in real time as the gait characteristic occurs;

wherein the determining the gait characteristic of the user comprises:

determining a Fourier transformation of a motion sensor signal;

comparing an amplitude of at least one frequency of said Fourier transformation with amplitudes of other frequencies of said Fourier transformation; wherein the at least one frequency is greater than 0 Hz and less than a threshold, and wherein the other frequencies are greater than the at least one frequency; wherein the threshold is greater than 0 Hz and less than 1 Hz;

filtering the motion sensor signal leveraging a wavelet transformation; and applying an autocorrelation to the motion sensor signal after the filtering.

82. The non-transitory processor-readable medium of claim 81, wherein the determining the gait characteristic is performed with an update frequency greater than the user's step frequency; and wherein the controlling the aspect of the application is performed with an update frequency greater than the user's step frequency.

83. The non-transitory processor-readable medium of claim 81, wherein the controlling the aspect of the application comprises controlling an aspect of a virtual environment.

84. The non-transitory processor-readable medium of claim 81, wherein the determining the gait characteristic leverages an accelerometer with three axes; and wherein the determining the gait characteristic further comprises:

identifying two of the accelerometer axes whose means have lowest absolute values;

determining for each one of the two identified axes an average of strongest frequency components;

classifying the two identified axes by leveraging the determined for each one of the two identified axes average of strongest frequency components;

comparing the two identified axes in terms of a current strength in a frequency band around a previously determined frequency; wherein the comparing leverages the classifying;

retrieving a time history of values of the two identified axes, wherein the values are in the frequency band around the previously determined frequency;

comparing the two identified axes in terms of a strength at an oldest time instant of the retrieved time history of values, wherein the values are in the frequency band around the previously determined frequency;

comparing a current strength of a first of the two identified axes in said frequency band with an average strength of said first of the two identified axes in said frequency band; wherein said average strength of said first of the two identified axes is determined over the retrieved time history of values; and comparing a current strength of a second of the two identified axes in said frequency band with an average strength of said second of the two identified axes in said frequency band; wherein said average strength of said second of the two identified axes is determined over the retrieved time history of values.

85. The non-transitory processor-readable medium of claim 84, wherein the determining the gait characteristic is performed with an update frequency greater than the user's step frequency; and wherein the controlling the aspect of the application is performed with an update frequency greater than the user's step frequency.

86. The non-transitory processor-readable medium of claim 84, wherein the controlling the aspect of the application comprises controlling an aspect of a virtual environment.

87. The non-transitory processor-readable claim 86, wherein the determining the gait characteristic is performed with an update frequency greater than the user's step frequency; and wherein the controlling the aspect of the application is performed with an update frequency greater than the user's step frequency.

88. The non-transitory processor-readable medium of claim 81, wherein the filtering leverages the threshold.

89. A non-transitory processor-readable medium including instructions which, when executed by one or more processors, cause the one or more processors to perform functions comprising:

determining a gait characteristic of a user of a mobile or wearable device in real time as the gait characteristic occurs; wherein the mobile or wearable device is carried by the user; and controlling an aspect of an application in the mobile or wearable device with the determined gait characteristic in real time as the gait characteristic occurs;

wherein the determining the gait characteristic leverages an accelerometer with three axes; and wherein the determining the gait characteristic comprises:

identifying two of the accelerometer axes whose means have lowest absolute values; and determining for each one of the two identified axes an average of strongest frequency components.

90. The non-transitory processor-readable medium of claim 89, wherein the determining the gait characteristic is performed with an update frequency greater than the user's step frequency; and wherein the controlling the aspect of the application is performed with an update frequency greater than the user's step frequency.

91. The non-transitory processor-readable medium of claim 89, wherein the controlling the aspect of the application comprises controlling an aspect of a virtual environment.

92. The non-transitory processor-readable medium of claim 89, wherein the strongest frequency components are recorded over a time window.

93. The non-transitory processor-readable medium of claim 89, wherein the determining the gait characteristic of the user further comprises: classifying the two identified axes by leveraging an indication determined for each one of the two identified axes; wherein the indication leverages the determined average of strongest frequency components.

94. The non-transitory processor-readable medium of claim 89, wherein the determining the gait characteristic of the user further comprises: classifying the two identified axes by leveraging the determined for each one of the two identified axes average of strongest frequency components.

95. The non-transitory processor-readable medium of claim 94, wherein the determining the gait characteristic of the user further comprises: comparing the two identified axes in terms of a current strength in a frequency band around a previously determined frequency; wherein the comparing leverages the classifying.

96. The non-transitory processor-readable medium of claim 95, wherein the determining the gait characteristic of the user further comprises: retrieving a time history of values of the two identified axes, wherein the values are in the frequency band around the previously determined frequency.

97. The non-transitory processor-readable medium of claim 96, wherein the determining the gait characteristic of the user further comprises: comparing the two identified axes in terms of a strength at an oldest time instant of the retrieved time history of values, wherein the values are in the frequency band around the previously determined frequency.

98. The non-transitory processor-readable medium of claim 97, wherein the determining the gait characteristic of the user further comprises: comparing a current strength of a first of the two identified axes in said frequency band with an average strength of said first of the two identified axes in said frequency band; wherein said average strength of said first of the two identified axes is determined over the retrieved time history of values.

99. The non-transitory processor-readable medium of claim 98, wherein the determining the gait characteristic of the user further comprises: comparing a current strength of a second of the two identified axes in said frequency band with an average strength of said second of the two identified axes in said frequency band; wherein said average strength of said second of the two identified axes is determined over the retrieved time history of values.

* * * * *